(12) United States Patent
Wada et al.

(10) Patent No.: US 8,506,853 B2
(45) Date of Patent: Aug. 13, 2013

(54) COMPOSITION FOR OPTICAL MATERIALS

(75) Inventors: Kenji Wada, Shizuoka (JP); Kyohei Arayama, Shizuoka (JP); Akiyoshi Goto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/904,252

(22) Filed: Oct. 14, 2010

(65) Prior Publication Data

US 2011/0089385 A1    Apr. 21, 2011

(30) Foreign Application Priority Data

Oct. 16, 2009  (JP) .................................. 2009-239462

(51) Int. Cl.
*F21V 9/04* (2006.01)
*C08F 30/08* (2006.01)
*C07F 7/00* (2006.01)

(52) U.S. Cl.
USPC ............................ 252/589; 526/279; 556/460

(58) Field of Classification Search
USPC ................. 252/589; 526/279; 556/460, 437, 556/422; 528/34, 33, 25, 28
See application file for complete search history.

(56) References Cited

U.S. PATENT DOCUMENTS

| | | | |
|---|---|---|---|
| 4,424,297 A * | 1/1984 | Bey | 524/714 |
| 2004/0120915 A1 | 6/2004 | Yang et al. | |
| 2005/0049381 A1 * | 3/2005 | Yamahiro et al. | 528/10 |
| 2008/0213602 A1 | 9/2008 | Morita et al. | |

FOREIGN PATENT DOCUMENTS

| | | |
|---|---|---|
| JP | 2000334881 * | 12/2000 |
| JP | 2004-021036 A | 1/2001 |
| JP | 2007-031619 A | 2/2007 |
| JP | 2007-254506 A | 10/2007 |
| JP | 2008-214455 A | 9/2008 |
| WO | 2006/132656 A2 | 12/2006 |

OTHER PUBLICATIONS

Office Action dated Apr. 30, 2013 in Japanese Application No. 2009-239462.

* cited by examiner

*Primary Examiner* — Ling Choi
*Assistant Examiner* — Monique Peets
(74) *Attorney, Agent, or Firm* — Sughrue Mion, PLLC

(57) ABSTRACT

The composition for optical materials includes a polymer obtained from silsesquioxanes which are represented by average composition formula (1): $(R^1SiO_{1.5})_x(R^2SiO_{1.5})_y$ (wherein $R^1$ is a polymerizable group, $R^2$ is a non-polymerizable group, x is a number of 2.0 to 14.0, y is a number of 2.0 to 14.0, provided that x+y=8.0 to 16.0, and $R^1$ groups and $R^2$ groups may be the same or different) and include at least one cage silsesquioxane compound. This composition is suitable for use as the antireflective film in optical devices, has less film shrinkage in the curing step, has good coated surface state and excellent moisture resistance and adhesion, has small changes in the refractive index under high temperature conditions, and is capable of forming a low-refractive-index film.

20 Claims, No Drawings

COMPOSITION FOR OPTICAL MATERIALS

TECHNICAL FIELD

The present invention relates to a composition for optical materials and more specifically to a composition capable of forming a low-refractive-index film which has a suitable and uniform thickness and is useful as an antireflective film in optical devices.

In laser annealing and a photoresist step for manufacturing various display panels (e.g., liquid crystal display panels, cold cathode tube panels, and plasma display panels), solid-state image sensors (e.g., charge-coupled devices (CCDs) and complementary metal oxide semiconductors (CMOSs)), optical devices (e.g., solar cell panels) as well as thin-film transistors and monocrystalline thin-film silicon solar cells, antireflective films have been used to improve the light focusing rate and further image quality while preventing external light reflection.

These antireflective films are classified based on the theory of antireflection optics into a multilayer type in which a high-refractive-index layer made of a metal oxide and a low-refractive-index layer are stacked on a substrate; and a monolayer type in which a low-refractive-index layer made of, for example, an organic fluorine compound or an inorganic compound is only formed thereon. In both the layer types, low-refractive-index materials in the form of a cured film having excellent scratching resistance, coatability and durability have been desired. In cases where a film is used particularly as the antireflective film in optical devices such as image sensors, the antireflective film is exposed to high temperatures of 200° C. or more for a long period of time and is therefore required to exhibit high heat resistance and temporal stability of the refractive index under high temperature conditions.

Various low-refractive-index materials have been heretofore proposed. For example, JP 2004-21036 A describes preparation of a low-reflective-index material using a hydrolytic condensation product of an alkoxysilane. JP 2008-214455 A discloses a composition for use in forming an antireflective film which contains a predetermined amount of cage silsesquioxane polymer.

SUMMARY OF THE INVENTION

However, in cases where the alkoxysilane hydrolytic condensation product as described in JP 2004-21036 A is used, a reaction proceeds between silanol groups remaining in the hydrolytic condensation product during the baking in the film forming process, which may cause the film shrinkage to proceed to develop cracks while deteriorating the film-forming properties. The remaining silanol groups facilitate the moisture adsorption, as a result of which the refractive index will change with time. In addition, the refractive index of the resulting film is not necessarily at a satisfactory level in practical use and the refractive index is to be further reduced.

The inventors of the invention prepared a film using a polymer obtained from a cage silsesquioxane specifically disclosed in JP 2008-214455 A which includes 8 $H_2C=CH-Si(O_{0.5})_3$ units and has a carbon-carbon double bond in every silicon atom and exposed the resulting film to a high temperature of 200° C. or more, and found that the refractive index changes with time. As described above, excellent temporal stability of the refractive index is required under high temperature conditions to use the film as the antireflective film in optical devices such as image sensors, and therefore further improvements have been required. The adhesion between the resulting film and the substrate was also not sufficient and further improvements on the moisture resistance of the resulting film have also been required.

In view of the situation as described above, an object of the present invention is to provide a composition for optical materials which is suitable for use as the antireflective film in optical devices, has less film shrinkage in the curing step, has good coated surface state and excellent moisture resistance and adhesion, has small changes in the refractive index under high temperature conditions, and is capable of forming a low-refractive-index film. Another object of the invention is to provide an antireflective film manufactured using the composition for optical materials. Still another object of the invention is to provide an optical device having the antireflective film.

The inventors of the invention have made an intensive study on the prior art techniques and as a result found that the above objects are achieved by using polymers obtained from silsesquioxanes which comprise a cage silsesquioxane (polyhedral oligomeric silsesquioxane) and satisfies a predetermined average composition. The present invention has been thus completed.

Accordingly, it was found that the above objects are achieved by the following means.

(1) A composition for optical materials comprising a polymer obtained from silsesquioxanes which are represented by average composition formula (1):

$$(R^1SiO_{1.5})_x(R^2SiO_{1.5})_y \qquad \text{Formula (1)}$$

(wherein $R^1$ is a polymerizable group, $R^2$ is a non-polymerizable group, x is a number of 2.0 to 14.0, y is a number of 2.0 to 14.0, provided that x+y=8.0 to 16.0, and $R^1$ groups and $R^2$ groups may be the same or different) and comprise at least one cage silsesquioxane compound.

(2) The composition for optical materials according to (1), wherein the at least one cage silsesquioxane compound is represented by formula (2):

$$(RSiO_{1.5})_a \qquad \text{Formula (2)}$$

wherein each R is independently a polymerizable group or a non-polymerizable group, a is an integer of 8, 10, 12, 14 or 16, provided that R groups may be the same or different.

(3) The composition for optical materials according to (2), wherein the silsesquioxanes comprise the at least one cage silsesquioxane compound selected from the group consisting of cage silsesquioxane compounds represented by general formulas (Q-1) to (Q-7):

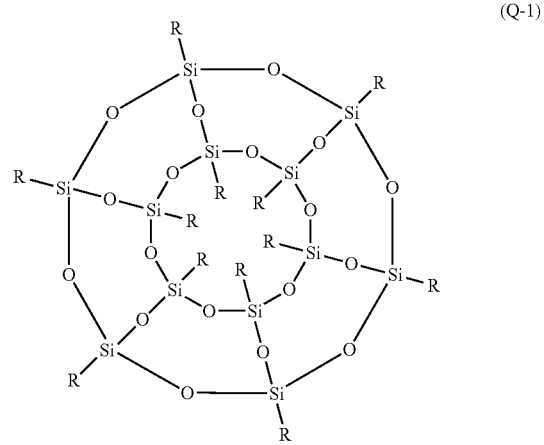

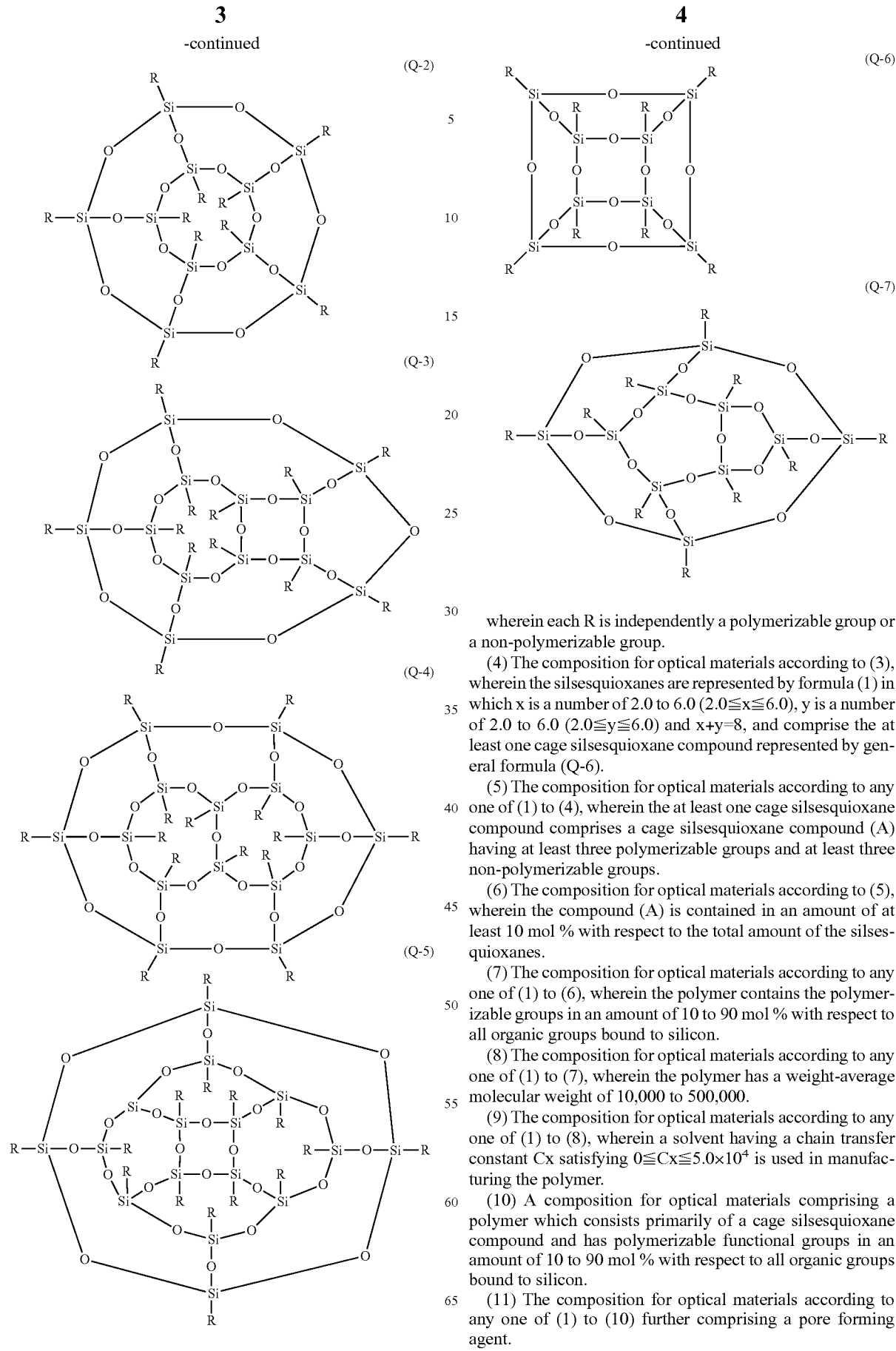

wherein each R is independently a polymerizable group or a non-polymerizable group.

(4) The composition for optical materials according to (3), wherein the silsesquioxanes are represented by formula (1) in which x is a number of 2.0 to 6.0 ($2.0 \leqq x \leqq 6.0$), y is a number of 2.0 to 6.0 ($2.0 \leqq y \leqq 6.0$) and x+y=8, and comprise the at least one cage silsesquioxane compound represented by general formula (Q-6).

(5) The composition for optical materials according to any one of (1) to (4), wherein the at least one cage silsesquioxane compound comprises a cage silsesquioxane compound (A) having at least three polymerizable groups and at least three non-polymerizable groups.

(6) The composition for optical materials according to (5), wherein the compound (A) is contained in an amount of at least 10 mol % with respect to the total amount of the silsesquioxanes.

(7) The composition for optical materials according to any one of (1) to (6), wherein the polymer contains the polymerizable groups in an amount of 10 to 90 mol % with respect to all organic groups bound to silicon.

(8) The composition for optical materials according to any one of (1) to (7), wherein the polymer has a weight-average molecular weight of 10,000 to 500,000.

(9) The composition for optical materials according to any one of (1) to (8), wherein a solvent having a chain transfer constant Cx satisfying $0 \leqq Cx \leqq 5.0 \times 10^4$ is used in manufacturing the polymer.

(10) A composition for optical materials comprising a polymer which consists primarily of a cage silsesquioxane compound and has polymerizable functional groups in an amount of 10 to 90 mol % with respect to all organic groups bound to silicon.

(11) The composition for optical materials according to any one of (1) to (10) further comprising a pore forming agent.

(12) The composition for optical materials according to (11), wherein the pore forming agent is at least one selected from the group consisting of polystyrene, polyalkylene oxide, polylactic acid, polycaprolactone, polycaprolactam, polyurethane, polyacrylate, polyacrylic acid, polymethacrylate, polymethacrylic acid, polyacetal and polyperoxide.

(13) The composition for optical materials according to (11) or (12), wherein the pore forming agent has a 50% weight loss temperature of 180 to 350° C. in thermogravimetric analysis under a nitrogen stream at a temperature elevation rate of 20° C./min.

(14) The composition for optical materials according to any one of (11) to (13), wherein the pore forming agent has a polystyrene-equivalent number-average molecular weight of 100 to 50,000.

(15) A film obtained using the composition for optical materials according to any one of (1) to (14).

(16) The film according to (15) having a refractive index of up to 1.34.

(17) The film according to (15) or (16) having a film density of 0.7 to 1.25 g/cm$^3$.

(18) The film according to any one of (15) to (17) used as an antireflective film.

(19) An optical device having the film according to any one of (15) to (18).

The present invention can provide a composition for optical materials which is suitable for use as the antireflective film in optical devices, has less film shrinkage in the curing step, has good coated surface state and excellent moisture resistance and adhesion, has small changes in the refractive index under high temperature conditions, and is capable of forming a low-refractive-index film. The present invention can also provide an antireflective film manufactured using the composition for optical materials and an optical device having the antireflective film.

DETAILED DESCRIPTION OF THE INVENTION

The composition for optical materials and the film obtained from the composition according to the invention are described below in detail.

The composition for optical materials according to the invention contains a polymer of any of silsesquioxanes which satisfy average composition formula described below and comprise at least one cage silsesquioxane compound. The composition is characterized by the inclusion of the polymer having a predetermined number of polymerizable groups. The number of polymerizable groups included in the polymer is smaller than that included in the above-described prior art polymer obtained from a cage silsesquioxane having 8 $H_2C=CH-Si(O_{0.5})_3$ units. Therefore, the number of polymerizable groups remaining after film curing is smaller, thus leading to the suppression of the reaction between the functional groups within the resulting film under exposure to high temperatures and the suppression of the changes in refractive index. In addition, since the polymer included in the composition is manufactured by polymerizing silsesquioxanes containing a smaller number of polymerizable groups than prior art polymers, the number of binding between recurring units is smaller and the polymer itself has a higher mobility in the solution or in the film, thus enabling a film having a large number of smaller pores to be manufactured.

In cases where the composition for optical materials of the invention further contains a pore forming agent, the composition exhibits a lower refractive index than conventional film materials, enabling a film having less reduction of the film thickness during the film curing to be manufactured. In other words, a balance between the low refractive index and film forming properties which has heretofore been difficult to achieve can be struck at a high level.

The silsesquioxanes which are used as the starting materials of the polymer included in the composition are first described. Then, the polymers manufactured from the silsesquioxanes and their manufacturing methods are described in detail.

(Silsesquioxanes)

The silsesquioxanes which are used as the starting materials of the polymer used in the invention are represented by average composition formula (1):

$(R^1SiO_{1.5})_x(R^2SiO_{1.5})_y$          Formula (1)

(wherein $R^1$ is a polymerizable group, $R^2$ is a non-polymerizable group, x is a number of 2.0 to 14.0 ($2.0 \leq x \leq 14.0$), y is a number of 2.0 to 14.0 ($2.0 \leq y \leq 14.0$), provided that x+y=8 to 16, and $R^1$ groups and $R^2$ groups may be the same or different) and include at least one cage silsesquioxane compound.

Silsesquioxane refers to a compound having a structure wherein each silicon atom is bonded to three oxygen atoms, and each oxygen atom is bonded to two silicon atoms (namely, a structure represented by $RSiO_{1.5}$ in which the ratio of the number of oxygen atoms to the number of silicon atoms is 1.5). More specifically, $RSiO_{1.5}$ units are covalently linked together through oxygen atoms in the units. The term "cage structure" as used herein means a structure which has a cavity that is defined by a plurality of rings formed of covalently bonded atoms and in which any point positioned within the cavity cannot leave the cavity without passing through the rings.

The silsesquioxanes of the invention comprise at least one cage silsesquioxane compound and therefore the film obtained from the resulting polymer has a lower refractive index while exhibiting excellent heat resistance and moisture resistance. In cases where two or more cage silsesquioxane compounds are used, two compounds of the same cage shape may be used or the compounds used may have different cage shapes.

In formula (1), $R^1$ is a polymerizable group. The polymerizable group is not particularly limited and examples thereof include a radical polymerizable group and a cationic polymerizable group. More specifically, cationic polymerizable groups such as epoxy group, oxetanyl group, oxazolyl group and vinyloxy group, and radical polymerizable groups such as alkenyl group, alkynyl group, acrylic acid ester, methacrylic acid ester, acrylamide, methacrylamide, vinyl ether and vinyl ester are preferred. Of these, radical polymerizable groups are preferred and alkenyl group and alkynyl group are more preferred because the synthesis is easy to perform and the polymerization reaction proceeds favorably.

Examples of the alkenyl group include those having a double bond at any position of an alkyl group, a cycloalkyl group, an aryl group, an aralkyl group, an alkoxy group and a silicon atom-containing group. Of these, groups having 1 to 12 carbon atoms are preferred and groups having 1 to 6 carbon atoms are more preferred. Exemplary alkenyl groups include vinyl group and allyl group. Vinyl group is preferred in terms of ease of polymerization control and mechanical strength.

Examples of the alkynyl group include those having a triple bond at any position of an alkyl group, a cycloalkyl group, an aryl group, an aralkyl group, an alkoxy group and a silicon atom-containing group. Of these, groups having 1 to 12 carbon atoms are preferred and groups having 1 to 6 carbon atoms are more preferred. Ethynyl group is preferred in terms of ease of polymerization control.

$R^2$ is a non-polymerizable group. The non-polymerizable group refers to a group which does not have polymerizability as described above. Illustrative examples thereof include an alkyl group, a cycloalkyl group, an aryl group, an aralkyl group, an alkoxy group and a silicon atom-containing group, and groups that are combinations thereof. Of these, an alkyl group, a cycloalkyl group and an aryl group are preferred from the viewpoint that the resulting film has a low refractive index and good heat resistance.

The alkyl group may have a substituent and is preferably a linear or branched alkyl group having 1 to 20 carbon atoms. The alkyl chain may contain oxygen atom, sulfur atom, nitrogen atom or a halogen atom. Illustrative examples of the alkyl group include linear alkyl groups such as methyl group, ethyl group, n-propyl group, n-butyl group, n-pentyl group, n-hexyl group, n-octyl group, n-dodecy group, n-tetradecyl group and n-octadecyl group; and branched alkyl groups such as isopropyl group, isobutyl group, t-butyl group, neopentyl group and 2-ethylhexyl group.

A preferred embodiment of the alkyl group is an alkyl group having fluorine atom (fluorinated alkyl group) from the viewpoint that the resulting film has a lower refractive index. The fluorinated alkyl group is one having hydrogen atoms partially or completely substituted with fluorine atoms. Illustrative examples thereof include trifluoromethyl group, pentafluoroethyl group, heptafluoropropyl group and nonafluorobutyl group.

The cycloalkyl group may have a substitutent and is preferably a cycloalkyl group having 3 to 20 carbon atoms. The cycloalkyl group may be polycyclic and have oxygen atom in the ring. Illustrative examples thereof include cyclopropyl group, cyclopentyl group, cyclohexyl group, norbornyl group and adamantyl group.

The aryl group may have a substituent and is preferably an aryl group having 6 to 14 carbon atoms. Examples thereof include phenyl group and naphthyl group.

The aralkyl group may have a substituent and is preferably an aralkyl group having 7 to 20 carbon atoms. Examples thereof include benzyl group, phenethyl group, naphthylmethyl group and naphthylethyl group.

The alkoxy group may have a substituent and is preferably an alkoxy group having 1 to 20 carbon atoms. Examples thereof include methoxy group, ethoxy group, propoxy group, n-butoxy group, pentyloxy group, hexyloxy group and heptyloxy group.

The silicon atom-containing group is not particularly limited as long as it contains silicon and a group represented by general formula (3):

*-L$^1$-Si—(R$^{20}$)$_3$   (3)

(wherein * represents the position of binding with silicon atom, L$^1$ is a divalent linkage group selected from an alkylene group, —O—, —S—, —Si(R$^{21}$)(R$^{22}$)—, —(R$^{23}$)— and combinations thereof. L$^1$ is preferably a divalent linkage group selected from an alkylene group, —O—, and combinations thereof.

The alkylene group preferably has 1 to 12 carbon atoms and more preferably 1 to 6 carbon atoms. $R^{21}$, $R^{22}$, $R^{23}$ and $R^{20}$ are each independently an alkyl group, a cycloalkyl group, an aryl group or an alkoxy group. The alkyl group, cycloalkyl group, aryl group and alkoxy group represented by $R^{21}$, $R^{22}$, $R^{23}$ and $R^{20}$ are as defined above, and methyl group, ethyl group, butyl group and cyclohexyl group are preferred.

Examples of the silicon atom-containing group that may be preferably used include silyloxy groups (trimethylsilyloxy, triethylsilyloxy and t-butyldimethylsilyloxy).

In formula (1), x is a number of 2.0 to 14.0. From the viewpoint that the resulting film has a lower refractive index while exhibiting more excellent heat resistance, light resistance and curing properties, x is preferably at least 2.5 and more preferably at least 3.0, but is preferably up to 11.5, more preferably up to 10.0, even more preferably up to 9.5, still more preferably up to 5.0 and most preferably up to 4.5.

In formula (1), y is a number of 2.0 to 14.0. From the viewpoint that the resulting film has a lower refractive index while exhibiting more excellent heat resistance and coating properties, y is preferably at least 3.0 and more preferably at least 5.5 but is preferably up to 12.0, more preferably up to 11.5, even more preferably up to 10.0, still more preferably up to 9.5, particularly preferably up to 7.5 and most preferably up to 5.0.

In formula (1), x plus y equals 8 to 16. From the viewpoint that the resulting film has a lower refractive index while exhibiting more excellent heat resistance, hygroscopicity and storage stability, x plus y preferably equals 8 to 14, more preferably 8 to 12 and even more preferably 8 to 10.

In addition, the ratio of x to y (x/y) in formula (1) preferably satisfies the relation: $0.2 \leqq x/y \leqq 2.5$. From the viewpoint that the resulting film has a lower refractive index while exhibiting more excellent heat resistance and mechanical strength, $0.2 \leqq x/y \leqq 2.0$ is more preferred and $0.3 \leqq x/y \leqq 2.0$ is even more preferred.

(Cage Silsesquioxane Compound)

The above-described silsesquioxanes satisfying average composition formula (1) comprise at least one cage silsesquioxane compound.

The cage silsesquioxane compound is not particularly limited as long as it has a cage structure formed by connecting m $RSi(O_{0.5})_3$ units together through covalent oxygen atoms.

From the viewpoint that the resulting film has a lower refractive index while exhibiting more excellent heat resistance, a cage silsesquioxane compound represented by formula (2):

(RSiO$_{1.5}$)$_a$   Formula (2)

(wherein each R is independently a polymerizable group or a non-polymerizable group) is preferred. The polymerizable group and the non-polymerizable group are as defined above. However, R groups may be the same or different.

In formula (2), a is an integer of 8, 10, 12, 14 or 16. In particular, a is preferably 8 or 10 from the viewpoint that the resulting film has a lower refractive index while exhibiting more excellent heat resistance, and a is more preferably 8 in terms of polymerization control.

In a preferred embodiment, the cage silsesquioxane is represented by any of general formulas (Q-1) to (Q-7). Of these, a compound represented by general formula (Q-6) is most preferred in terms of availability, polymerization control and solubility.

(Q-1)
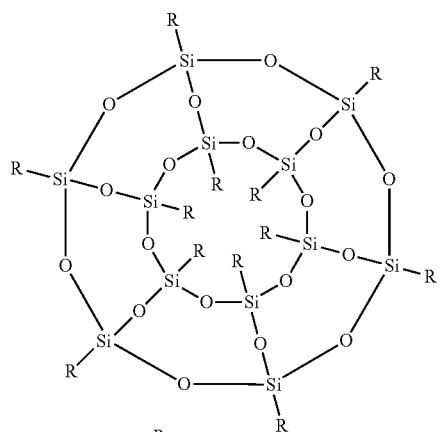

(Q-2)
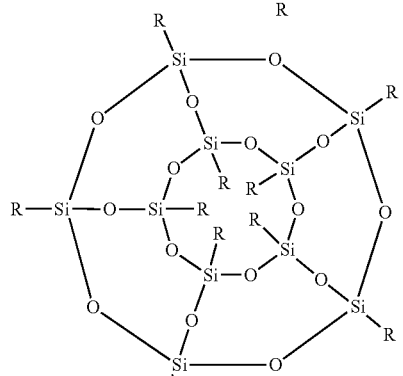

(Q-3)
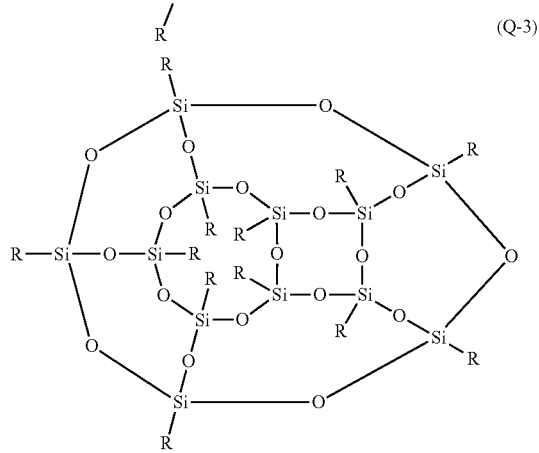

(Q-4)
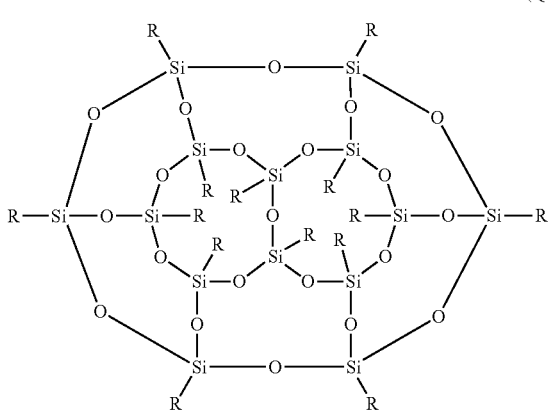

(Q-5)
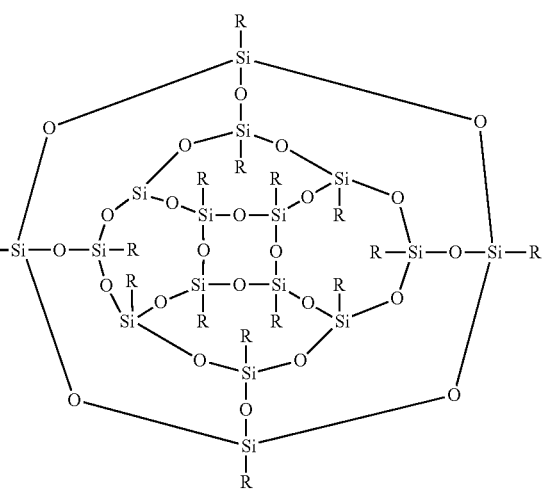

(Q-6)
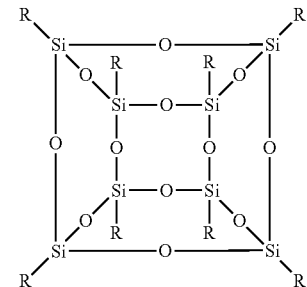

(Q-7)
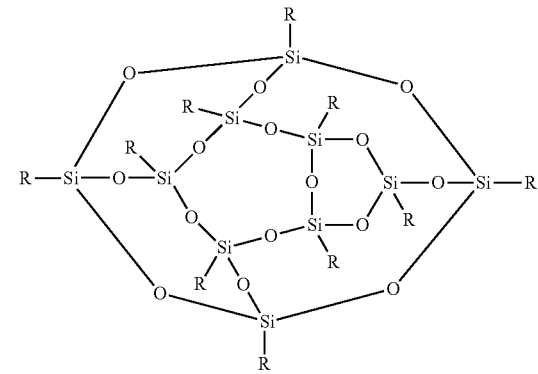

In general formulas (Q-1) to (Q-7), each R is independently a polymerizable group or a non-polymerizable group.

(Preferred Embodiments of Silsesquioxanes)

In a preferred embodiment, the silsesquioxanes are represented by formula (1) wherein x is a number of 2.0 to 6.0 ($2.0 \leq x \leq 6.0$) and preferably 3.0 to 4.5 ($3.0 \leq x \leq 4.5$), y is a number of 2.0 to 6.0 ($2.0 \leq y \leq 6.0$) and preferably 3.5 to 5.0 ($3.5 \leq y \leq 5.0$), x+y=8, and comprise at least one cage silsesquioxane compound represented by general formula (Q-6).

The silsesquioxanes comprise at least one cage silsesquioxane compound (T8 type) represented by general formula (Q-6). The silsesquioxanes may comprise a mixture of a cage silsesquioxane compound having three polymerizable groups and five non-polymerizable groups, and a cage silsesquioxane compound having four polymerizable groups and four non-polymerizable groups.

In another preferred embodiment, the silsesquioxanes are represented by formula (1) wherein x is a number of 2.0 to 8.0

(2.0≦x≦8.0) and preferably 3.0 to 4.5 (3≦x≦4.5), y is a number of 2.0 to 8.0 (2.0≦y≦8.0) and preferably 5.5 to 7.0 (5.5≦y≦7.0), x+y=10, and comprise a cage silsesquioxane compound represented by general formula (Q-2) and/or a cage silsesquioxane compound represented by general formula (Q-7).

The silsesquioxanes comprise at least one cage silsesquioxane compound (T10 type) represented by general formula (Q-2) or (Q-7).

In still another preferred embodiment, the silsesquioxanes are represented by formula (1) wherein x is a number of 2.0 to 10.0 (2.0≦x≦10.0) and preferably 3.0 to 5.0 (3.0≦x≦5.0), y is a number of 2.0 to 10.0 (2.0≦y≦10.0) and preferably 7.0 to 9.0 (7.0≦y≦9.0), x+y=12, and comprise a cage silsesquioxane compound represented by general formula (Q-1) and/or a cage silsesquioxane compound represented by general formula (Q-3).

The silsesquioxanes comprise at least one cage silsesquioxane compound (T12 type) represented by general formula (Q-1) or (Q-3).

In yet another preferred embodiment, the silsesquioxanes are represented by formula (1) in which x is a number of 2.0 to 12.0 (2.0≦x≦12.0), y is a number of 2.0 to 12.0 (2.0≦y≦12.0) and x+y=14, and comprise a cage silsesquioxane compound represented by general formula (Q-4).

The silsesquioxanes comprise at least one cage silsesquioxane compound (T14 type) represented by general formula (Q-4).

In a further preferred embodiment, the silsesquioxanes comprise a cage silsesquioxane compound (A) having at least three polymerizable groups and at least three non-polymerizable groups. In other words, the compound (A) is one represented by formula (2) in which at least three R groups are polymerizable and at least three R groups are non-polymerizable. A cured film having a lower refractive index while exhibiting more excellent heat resistance can be obtained by incorporating the compound (A).

The cage silsesquioxane compound (A) should have at least three polymerizable groups and at least three non-polymerizable groups.

The structure of the compound (A) is not particularly limited but the compound (A) is preferably represented by any of general formulas (Q-1) to (Q-7).

For example, the compound (A) corresponds to a compound represented by general formula (Q-6) which has 3 to 5 polymerizable groups and 3 to 5 non-polymerizable groups so that the total number of the polymerizable groups and the non-polymerizable groups is 8.

The compound (A) corresponds to a compound represented by general formula (Q-2) or (Q-7) which has 3 to 7 polymerizable groups and 3 to 7 non-polymerizable groups so that the total number of the polymerizable groups and the non-polymerizable groups is 10.

The compound (A) corresponds to a compound represented by general formula (Q-4) which has 3 to 11 polymerizable groups and 3 to 11 non-polymerizable groups so that the total number of the polymerizable groups and the non-polymerizable groups is 14.

The content of the compound (A) with respect to the total amount of the silsesquioxanes is not particularly limited but is preferably at least 10 mol %, more preferably 20 to 100 mol % and even more preferably 60 to 100 mol % with respect to the total amount of the silsesquioxanes in terms of more excellent properties of the resulting film. It is particularly preferred for the silsesquioxanes to be made up of only the compound (A) and to contain substantially no other cage silsesquioxane compound.

The above-described silsesquioxanes usually comprise at least one cage silsesquioxane compound but may contain other polysiloxane compounds such as ladder silsesquioxane compounds as long as the merits of the invention are not impaired.

Specific examples of the silsesquioxanes are described below but the invention is not limited thereto. The substituent ratio in Table 1 corresponds to x/y in formula (1).

TABLE 1

| Compound | Cage structure | Substituent $R^1$ | Substituent $R^2$ | Substituent Ratio ($R^1/R^2$) |
|---|---|---|---|---|
| I-1 | Q-1 | vinyl | methyl | 6.0/6.0 |
| I-2 | Q-1 | vinyl | methyl | 3.0/9.0 |
| I-3 | Q-1 | vinyl | phenyl | 6.0/6.0 |
| I-4 | Q-2 | vinyl | methyl | 5.0/5.0 |
| I-5 | Q-3 | vinyl | dodecyl | 6.0/6.0 |
| I-6 | Q-4 | 4-viniyphenyl | ethyl | 4.0/10.0 |
| I-7 | Q-5 | ethynyl | methyl | 4.5/11.5 |
| I-8 | Q-6 | vinyl | methyl/phenyl | 2.5/3.5/2.0 |
| I-9 | Q-6 | vinyl | methyl | 2.5/5.5 |
| I-10 | Q-6 | vinyl | methyl | 3.0/5.0 |
| I-11 | Q-6 | vinyl | methyl | 3.5/4.5 |
| I-12 | Q-6 | vinyl | methyl | 3.9/4.1 |
| I-13 | Q-6 | vinyl | methyl | 4.0/4.0 |
| I-14 | Q-6 | vinyl | methyl | 4.4/3.6 |
| I-15 | Q-6 | vinyl | methyl | 5.0/3.0 |
| I-16 | Q-6 | vinyl | methyl | 5.5/2.5 |
| I-17 | Q-6 | ethynyl | methyl | 3.1/4.9 |
| I-18 | Q-6 | vinyl | phenyl | 4.0/4.0 |
| I-19 | Q-6 | 4-viniyphenyl | methyl | 2.0/6.0 |
| I-20 | Q-6 | 4-viniyphenyl/vinyl | methyl | 1.0/2.0/5.0 |
| I-21 | Q-6 | vinyl | pentafluorophenyl | 4.0/4.0 |
| I-22 | Q-6 | vinyl | $CF_3CH_2CH_2$— | 3.0/5.0 |
| I-23 | Q-6 | ($CH_2$=C($CH_3$)$CO_2$($CH_2$)$_3$—/vinyl | methyl | 1.0/3.0/4.0 |
| I-24 | Q-6 | ($CH_2$=CH)$Me_2$SiO— | $Me_3$SiO— | 4.0/4.0 |
| I-25 | Q-6 | vinyl | propyl | 4.0/4.0 |
| I-26 | Q-6 | vinyl | ethyl | 4.1/3.9 |
| I-27 | Q-6 | vinyl | ethyl | 4.3/3.7 |
| I-28 | Q-6 | allyl | cyclohexyl | 2.5/5.5 |
| I-29 | Q-6 | allyl/vinyl | methyl | 1.2/1.9/4.9 |

TABLE 1-continued

| Compound | Cage structure | Substituent R$^1$ | Substituent R$^2$ | Substituent Ratio (R$^1$/R$^2$) |
|---|---|---|---|---|
| I-30 | Q-6 | (CH$_2$=C(CH$_3$)CONH(CH$_2$)$_3$— | methyl | 4.0/4.0 |
| I-31 | Q-7 | ethynyl | phenyl | 3.0/7.0 |

Commercial products available from Aldrich and Hybrid Plastics, Inc. may be employed for the cage silsesquioxane compound used in the invention. Alternatively, the cage silsesquioxane compound may be synthesized by known methods described in Polymers, 20, 67-85, 2008; Journal of Inorganic and Organometallic Polymers, 11(3), 123-154, 2001; Journal of Organometallic Chemistry, 542, 141-183, 1997; Journal of Macromolecular Science A. Chemistry, 44(7), 659-664, 2007; Chem. Rev., 95, 1409-1430, 1995; Journal of Inorganic and Organometallic Polymers, 11(3), 155-164, 2001; Dalton Transactions, 36-39, 2008; Macromolecules, 37(23), 8517-8522, 2004; and Chem. Mater., 8, 1250-1259, 1996.

(Silsesquioxane Polymer)

The physical properties of the polymer obtained using any of the silsesquioxanes as the starting material and its manufacturing method are described below in detail.

The weight-average molecular weight (M$_w$) of the polymer is not particularly limited but is preferably $1.0 \times 10^4$ to $50 \times 10^4$, more preferably $3.5 \times 10^4$ to $40 \times 10^4$ and most preferably $5.0 \times 10^4$ to $35 \times 10^4$.

The number-average molecular weight (M$_n$) of the polymer is not particularly limited but is preferably $1.5 \times 10^4$ to $35 \times 10^4$, more preferably $1.5 \times 10^4$ to $20 \times 10^4$ and most preferably $2.5 \times 10^4$ to $15 \times 10^4$.

The Z+1 average molecular weight (M$_{Z+1}$) of the polymer is not particularly limited but is preferably $1.5 \times 10^4$ to $65 \times 10^4$, more preferably $2.5 \times 10^4$ to $50 \times 10^4$ and most preferably $3.5 \times 10^4$ to $35 \times 10^4$.

By setting the weight-average molecular weight and the number-average molecular weight within the above-defined ranges, the solubility in organic solvents and the filtering properties can be improved while suppressing generation of particles during the storage, thus enabling a film with a low refractive index having improved coated surface state to be formed.

In terms of the solubility in organic solvents, filtering properties and coated surface state, it is preferred for the polymer to be substantially free of a component with a molecular weight of at least 3,000,000, more preferably at least 2,000,000 and most preferably at least 1,000,000.

It is preferred for unreacted polymerizable groups derived from the cage silsesquioxane compound to remain in the polymer, more preferably in an amount of 10 to 90 mol %, even more preferably 20 to 90 mol % and most preferably 30 to 90 mol %. Within the above-defined range, the heat resistance, curing properties and mechanical strength of the resulting film are further improved.

These properties can be quantitatively determined by $^1$H-NMR spectroscopy.

The above-described polymer consists primarily of at least one cage silsesquioxane compound. The content of polymerizable groups in the polymer is not particularly limited but is preferably 10 to 90 mol %, more preferably 10 to 50 mol % and even more preferably 10 to 25 mol % with respect to all organic groups bound to silicon. Within the above-defined range, the heat resistance and mechanical strength of the resulting film are further improved.

The cage silsesquioxane structure is preferably included in the polymer in an amount of 10 to 100 wt % and more preferably 20 to 100 wt %. Within the above-defined range, the heat resistance and transparency of the resulting film are further improved while reducing the refractive index.

(Method of Manufacturing Polymer)

The polymer production method is not particularly limited and examples thereof include polymerization reaction of polymerizable groups and hydrosilylation reaction.

The polymerization reaction of polymerizable groups is not particularly limited and examples thereof include radical polymerization, cationic polymerization, anionic polymerization, ring-opening polymerization, polycondensation, polyaddition, addition condensation, and polymerization in the presence of a transition metal catalyst.

The hydrosilylation reaction may be performed by, for example, a method which involves dissolving the cage silsesquioxane compound(s) and a compound containing at least 2 SiH groups in the molecule (e.g., bis(dimethylsilyl)ethane, 1,1,3,3-tetramethyldisiloxane) in an organic solvent such as toluene or xylene and heating at 20 to 200° C. in the presence of a catalyst such as a platinum(0)-1,3-divinyl-1,1,3,3-tetramethyl disiloxane complex.

A polymerization reaction through polymerizable groups is a preferred method for producing the polymer and radical polymerization is most preferred. Exemplary synthesis processes include a batch polymerization process in which the silsesquioxanes and an initiator are dissolved in a solvent and heated for polymerization, a dropwise addition polymerization process (continuous addition) in which the silsesquioxanes are dissolved in a solvent and heated, and an initiator solution is added dropwise over 1 to 10 hours, and a divided addition polymerization process (divided addition) in which an initiator is added in several divided portions. In terms of further improved film strength and molecular weight reproducibility, divided addition and continuous addition are preferred.

The reaction temperature of the polymerization reaction is usually 0° C. to 200° C., preferably 40° C. to 170° C. and more preferably 80° C. to 160° C.

The reaction is preferably performed in an inert gas atmosphere such as nitrogen or argon in order to suppress the inactivation of the polymerization initiator due to oxygen. The oxygen concentration during the reaction is preferably up to 100 ppm, more preferably up to 50 ppm and most preferably up to 20 ppm.

The reaction solution during the polymerization contains the silsesquioxanes at a concentration of preferably up to 30 wt %, more preferably up to 20 wt %, even more preferably up to 15 wt % and most preferably up to 10 wt % with respect to the total weight of the reaction solution. The generation of impurities such as gelled components can be suppressed by setting the concentration within the above-defined range.

Any solvent may be used for the polymerization reaction as long as the silsesquioxanes can be dissolved therein at the required concentration and it does not adversely affect the properties of the film formed from the resulting polymer. In the following description, for example, an ester solvent refers to a solvent having an ester group in the molecule.

For example, solvents described in paragraph [0038] of JP 2008-218639 A may be used.

Of these, ester solvents, ether solvents and aromatic hydrocarbon solvents are preferably used. Illustrative examples of the solvents that may be preferably used include ethyl acetate, propyl acetate, isopropyl acetate, butyl acetate, pentyl acetate, hexyl acetate, methyl propionate, propylene glycol monomethyl ether acetate, tetrahydrofuran, diphenyl ether, anisole, toluene, xylene, mesitylene and t-butylbenzene. Ethyl acetate, butyl acetate, diphenyl ether, anisole, mesitylene and t-butylbenzene are particularly preferred. These may be used alone or in combination of two or more.

The solvent preferably has a boiling point of 65° C. or higher because the reaction solution can be heated to a temperature necessary to decompose the polymerization initiator during the reaction.

Of these solvents, it is particularly preferred to use a solvent having a chain transfer constant (Cx) larger than 0 but smaller than or equal to $5.0 \times 10^4$ ($0 \leq Cx \leq 5.0 \times 10^4$) in terms of easy polymerization control for the resulting polymer and more excellent properties of the resulting film.

In terms of easy polymerization control for the resulting polymer and more excellent properties of the resulting film, the solvent used preferably has a solubility parameter of 10 to 25 $MPa^{1/2}$ and more preferably 15 to 25 $MPa^{1/2}$. The solubility parameter as used herein is a value obtained using the method described in *Polymer Handbook Fourth Edition* Volume 2 (A John Wiley & Sons, Inc., Publication) J. BRANDRUP, E. H. IMMERGUT and E. A. GRULKE (1999), pp. 675-714.

The silsesquioxanes are preferably polymerized in the presence of a nonmetallic polymerization initiator. For example, free radicals such as carbon radical and oxygen radical can be formed by application of heat to thereby polymerize the silsesquioxanes in the presence of a polymerization initiator exhibiting activity.

It is particularly preferred to use organic peroxides or organic azo compounds for the polymerization initiator. Exemplary organic peroxides and organic azo compounds that may be used include those described in paragraphs [0033] to [0035] of JP 2008-239685 A.

In terms of the safety of the reagent itself and the molecular weight reproducibility in the polymerization reaction, the polymerization initiator is preferably an organic azo compound and is more preferably an azo ester compound such as V-601 with which harmful cyanogen is not incorporated in the polymer.

The 10-hour half-life temperature of the polymerization initiator is preferably 100° C. or less. At a 10-hour half-life temperature of 100° C. or less, it is easy for the polymerization initiator not to remain at the end of the reaction.

The polymerization initiators may be used alone or in combination of two or more.

The polymerization initiator is used in an amount of preferably 0.0001 to 2 mol, more preferably 0.003 to 1 mol and most preferably 0.001 to 0.5 mol per mol of the monomer.

The reaction solution after the polymerization reaction of the silsesquioxanes may be used as a coating solution without any further treatment but is preferably purified after the end of the reaction. Conventional purification processes may be applied as exemplified by liquid/liquid extraction processes in which residual monomers or oligomer components are removed by rinsing with water or by proper combinations of solvents; solution purification processes such as ultrafiltration, centrifugation and column chromatography in which substances having molecular weights below a specified value are only extracted and removed; reprecipitation processes in which a polymer solution is added dropwise to a poor solvent to solidify a polymer in the poor solvent to remove residual monomers and the like; and solid purification processes in which a polymer slurry separated by filtration is washed with a poor solvent.

For example, a solvent in which the polymer is poorly soluble or insoluble (poor solvent) is brought into contact with a polymer-containing solution in a volume up to 10 times and preferably 10 to 5 times as large as that of the reaction solution to deposit the polymer as a solid. The solvent used in the precipitation or reprecipitation operation from the polymer solution (precipitation or reprecipitation solvent) should be one in which the polymer is poorly soluble. A solvent may be appropriately selected according to the type of polymer from among hydrocarbons, halogenated hydrocarbons, nitro compounds, ethers, ketones, esters, carbonates, alcohols, carboxylic acids, water and solvent mixtures containing any of these solvents and used. Of these, the precipitation or reprecipitation solvent preferably contains at least an alcohol (particularly methanol) or water.

A polymerization inhibitor may be added to the silsesquioxane polymer during its preparation step in order to prevent the polymerization from proceeding more than necessary. Examples of the polymerization inhibitor include 4-methoxyphenol, 2,6-bis(1,1-dimethylethyl)-4-methylphenol and catechol.

(Composition for Optical Materials)

The composition for optical materials of the invention contains the polymer obtained from any of the silsesquioxanes represented by the predetermined average composition formula. The composition of the invention may be a solution containing the polymer dissolved in a solvent (e.g., organic solvent) or a solid containing the polymer.

The composition of the invention may be used in various applications and the content of polymer and the type of additives to be added are determined depending on the intended purpose. The inventive composition may be used, for example, to manufacture films (e.g., insulating films) or in low-refractive-index films, low-refractive-index materials, gas adsorption materials, and resist materials.

The content of the polymer in the composition is not particularly limited but when it is used for film formation to be described later, the polymer content is preferably at least 50 wt %, more preferably at least 60 wt % and even more preferably at least 70 wt % with respect to the total solids in the composition. The upper limit is 100 wt %. A film having an improved coated surface state can be formed at a higher polymer content in the solids. The expression "solids" as used herein refers to solids making up the film to be described later and no solvent is included.

The composition of the invention may contain a solvent. In other words, it is preferred for the polymer to be dissolved in a proper solvent and used by coating on a support.

It is preferred to use a solvent in which at least 5 wt % and more preferably at least 10 wt % of polymer dissolves at 25° C. More specifically, solvents described in paragraph [0044] of JP 2008-214454 A may be used.

Preferred examples of the solvent include propylene glycol monomethyl ether acetate, propylene glycol monomethyl ether, 2-heptanone, cyclohexanone, γ-butyrolactone, ethylene glycol monomethyl ether, ethylene glycol monoethyl ether, ethylene glycol monoethyl ether acetate, propylene glycol monomethyl ether, propylene glycol monoethyl ether, ethylene carbonate, butyl acetate, methyl lactate, ethyl lactate, methyl methoxypropionate, ethyl ethoxypropionate, N-methylpyrrolidone, N,N-dimethylformamide, tetrahydrofuran, methyl isobutyl ketone, xylene, mesitylene and diisopropylbenzene.

In cases where the composition contains a solvent, the total solid concentration in the composition is preferably 1 to 30 wt % with respect to the total amount of the composition and is appropriately adjusted depending on the intended use. Within the above range, the coated film has a suitable thickness and the coating solution exhibits more excellent storage stability.

The composition may contain a polymerization initiator. Particularly in cases where the composition is to be cured at a low temperature to form a film, the composition preferably contains the polymerization initiator. The type of polymerization initiator used in such a case is not particularly limited. An initiator that may trigger the polymerization by exposure to radiation may be used.

The composition preferably contains metals as impurities in a sufficiently small amount. The concentration of the metals in the composition may be measured by ICP-MS at a high sensitivity and the content of metals other than the transition metals in such a case is preferably up to 300 ppm and more preferably up to 100 ppm.

(Additives)

The composition may also contain additives such as a radical generator, a colloidal silica, a surfactant, an adhesion promoter and a pore forming agent as long as the properties (e.g., heat resistance, dielectric constant, mechanical strength, coatability and adhesion properties) of the film obtained using the composition are not impaired.

(Colloidal Silica)

The composition may contain any colloidal silica as long as it does not adversely affect the objects of the invention. Typically, the colloidal silica is in the form of a dispersion of a high-purity silicic anhydride in a hydrophilic organic solvent or water typically having an average particle size of 5 to 30 nm and preferably 10 to 20 nm and a solid concentration of about 5 to about 40 wt %.

[Surfactant]

The composition may contain any surfactant as long as it does not adversely affect the objects of the invention. Exemplary surfactants include nonionic surfactants, anionic surfactants and cationic surfactants as well as silicone surfactants, fluorine-containing surfactants, polyalkylene oxide surfactants and acrylic surfactants. These surfactants may be used alone or in combination of two or more. Among these, silicone surfactants, nonionic surfactants, fluorine-containing surfactants and acrylic surfactants are preferred and silicone surfactants are particularly preferred.

The surfactant is preferably used in the invention in an amount of 0.01 to 1 wt % and more preferably 0.01 to 0.5 wt % with respect to the total amount of the composition.

The term "silicone surfactant" as used herein means a surfactant containing at least one silicon atom. Although the silicone surfactant used is not particularly limited, use of a surfactant having a structure containing an alkylene oxide and dimethylsiloxane is preferable. The structure more preferably contains the moiety represented by the following chemical formula:

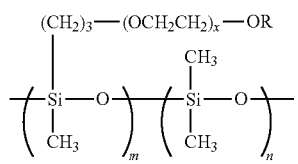

wherein R is hydrogen atom or an alkyl group having 1 to 5 carbon atoms, x is an integer of 1 to 20, and m and n are each independently an integer of 2 to 100. R groups may be the same or different.

Examples of the silicone surfactant that may be used include BYK306 and BYK307 (available from BYK Japan KK), SH7PA, SH21PA, SH28PA, and SH30PA (available from Dow Corning Toray Co., Ltd.), and Troysol 5366 (available from Troy Corporation).

The nonionic surfactant is not particularly limited. Exemplary nonionic surfactants include polyoxyethylene alkyl ethers, polyoxyethylene aryl ethers, polyoxyethylene dialkyl esters, sorbitan fatty acid esters, fatty acid-modified polyoxyethylenes, and polyoxyethylene-polyoxypropylene block copolymers.

The fluorine-containing surfactant is not particularly limited. Examples thereof include perfluorooctylpolyethylene oxide, perfluorodecylpolyethylene oxide, perfluorododecylpolyethylene oxide, PF656 (available from OMNOVA Solutions Inc.) and PF6320 (available from OMNOVA Solutions Inc.).

The acrylic surfactant is not particularly limited. Examples thereof include (meth)acrylic acid copolymers.

(Adhesion Promoter)

The composition may contain any adhesion promoter as long as it has no adverse effects on the objects of the invention. Examples of the adhesion promoter include 3-glycidyloxypropyltrimethoxysilane, 3-aminoglycidyloxypropyltriethoxysilane, 3-glycidyloxypropylmethyldimethoxysilane and 3-aminopropyltrimethoxysilane. Use may also be made of compounds described in paragraph [0048] of JP 2008-243945.

The adhesion promoter is preferably used in an amount of up to 10 wt % and particularly 0.05 to 5 wt % with respect to the total solids in the composition although the content is not particularly limited.

(Pore Forming Agent)

The composition of the invention may have a pore formation factor incorporated therein in a content that does not adversely affect the mechanical strength of the film to thereby produce a porous film having a low refractive index. There is no particular limitation on the pore forming agent serving as a pore forming factor, and a non-metallic compound is preferably used. The pore forming agent should simultaneously have the solubility in the solvent used in the coating solution and the compatibility with the resin for an insulating film or its precursor.

A polymer may also be used for the pore forming agent. Examples of the polymer that may be used for the pore forming agent include polyvinyl aromatic compounds (such as polystyrenes, polyvinylpyridines and halogenated polyvinyl aromatic compounds), polyacrylonitriles, polyalkylene oxides (polyethylene oxides and polypropylene oxides), polyethylenes, polylactic acids, polysiloxanes, polycaprolactones, polycaprolactams, polyurethanes, polymethacrylates (polymethyl methacrylates) or polymethacrylic acids, polyacrylates (polymethyl acrylates) and polyacrylic acids, polydienes (polybutadienes and polyisoprenes), polyvinyl chlorides, polyacetals, and amine-capped alkylene oxides, polyphenylene oxides, poly(dimethylsiloxanes), polytetrahydrofurans, polycyclohexylethylenes, polyethyloxazolines, polyvinylpyridines, and polycaprolactones.

Of these, polystyrenes, polyalkylene oxides, polylactic acids, polycaprolactones, polycaprolactams, polyurethanes, polyacrylates, polyacrylic acids, polymethacrylates, polymethacrylic acids, polyacetals and polyperoxides are preferred and polystyrenes, polymethacrylates, polyalkylene oxides and polyacetals are particularly preferred from the viewpoint that the resulting film has a lower refractive index and the cured film has a uniform surface.

Exemplary polystyrenes include anionic polymerizable polystyrenes, syndiotactic polystyrenes, unsubstituted and substituted polystyrenes (e.g., poly(Cx-methylstyrene)), and unsubstituted polystyrenes are preferred.

Exemplary polymethacrylates that may be preferably used include tertiary ester-containing polymethacrylates. Specific examples of the polymethacrylates include, but are not limited to, the following:

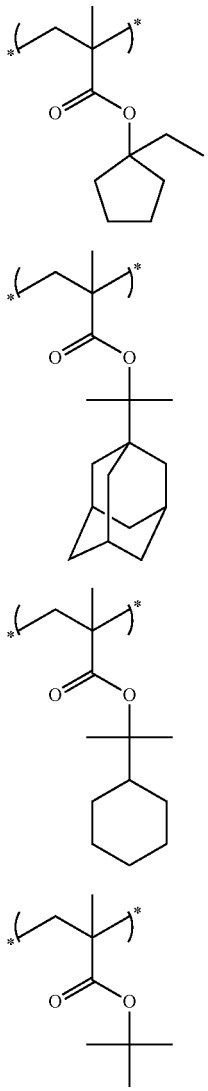

(B-1)

(B-2)

(B-3)

(B-4)

Exemplary polyalkylene oxides include polyethylene oxides, polyoxyethylene oxide alkyl ethers, polyethylene oxide alkyl esters, polypropylene oxides, polypropylene oxide alkyl ethers, polypropylene oxide alkyl esters, polyethylene oxide-polypropylene oxide copolymers, polyethylene oxide-polypropylene oxide alkyl ethers, polyethylene oxide-polypropylene oxide alkyl esters and polybutylene oxides.

Polyacetal may be a so-called polyacetal homopolymer obtained by the homopolymerization of formaldehyde, a polyacetal copolymer obtained by the polymerization of trioxane, a cyclic ether and/or a cyclic formal compound, or a polyacetal copolymer obtained by the polymerization of divinyl ether and a diol. Specific examples of the polyacetal include, but are not limited to, the following:

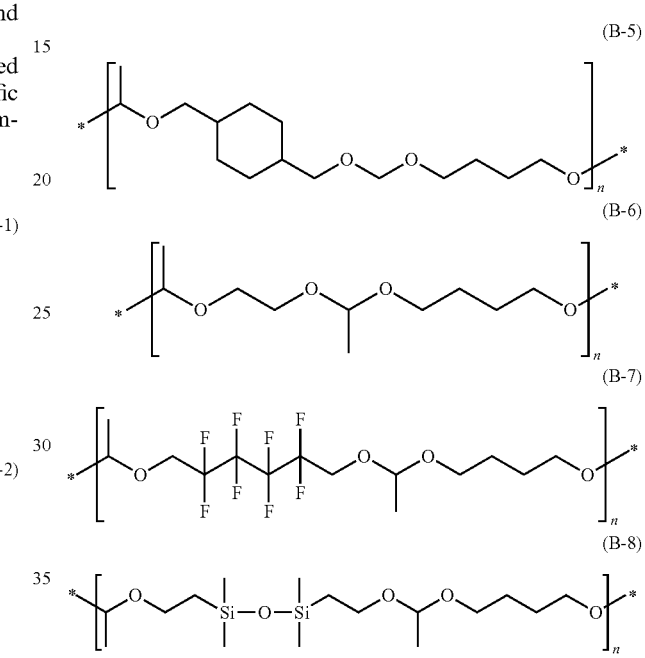

(B-5)

(B-6)

(B-7)

(B-8)

As for the boiling point or decomposition temperature of the pore forming agent, the 50% weight loss temperature in the thermogravimetric analysis under a nitrogen stream at a temperature elevation rate of 20° C./min is preferably from 180 to 350° C. and more preferably from 200 to 300° C. from the viewpoint that the resulting film has a lower refractive index and the film shrinkage during the curing is suppressed.

The polystyrene-equivalent number-average molecular weight of the pore forming agent is not particularly limited but is preferably from 100 to 50,000, more preferably from 100 to 30,000 and most preferably from 150 to 25,000 from the viewpoint that the phase separation in the film is suppressed and that a transparent film having no topographic features is obtained.

The amount of pore forming agent added is not particularly limited but is preferably from 0.5 to 50 wt %, more preferably from 1.0 to 40 wt % and most preferably from 5.0 to 30 wt % with respect to the total solids in the composition.

The method of producing the composition is not particularly limited and if a solvent may be included, the composition is obtained by adding a predetermined amount of polymer to the solvent and stirring the mixture.

The composition is preferably used for film formation after insoluble matter and gel-like components have been removed by filtration. The filter used preferably has a pore size of 0.05 to 2.0 µm, more preferably 0.05 to 1.0 µm and most preferably 0.05 to 0.5 µm. The film is preferably made of polytetrafluoroethylene, polyethylene, polypropylene or nylon, and more preferably made of polytetrafluoroethylene, polyethylene or nylon.

(Film-Forming Method)

The composition for optical materials according to the invention may be used for various applications. For example, the composition may be used to form an antireflective film.

The method of forming the antireflective film using the inventive composition for optical materials is not particularly limited, but the antireflective film can be formed by a process which involves applying the composition for optical materials to a substrate such as silicon wafer, $SiO_2$ wafer, SiN wafer, glass, plastic film or microlens by any method selected from, for example, spin coating, roller coating, dip coating, scan coating, spray coating and bar coating, optionally removing the solvent by heating treatment to form a film and curing the film.

Spin coating and scan coating are preferably used to apply the composition to the substrate. Spin coating is particularly preferred. Commercially available devices may be used for spin coating. Devices such as CLEAN TRACK Series available from Tokyo Electron Ltd., D-Spin Series available from Dainippon Screen Mfg. Co., Ltd. and SS Series and CS Series available from Tokyo Ohka Kogyo Co., Ltd. may be preferably used.

As for the condition of spin coating, any rotation speed may be employed. However, for coating a 300-mm silicone substrate, the rotation speed is preferably around 1300 rpm in view of in-plane uniformity of the formed film. The method for discharging the composition solution may be either dynamic discharge in which the composition solution is discharged onto a rotating substrate or static discharge in which the composition solution is discharged onto a stationary substrate. However, dynamic discharge is preferred in view of in-plane uniformity of the formed film. Alternatively, a method in which only the main solvent included in the composition is preliminarily discharged onto the substrate to form a liquid film and then the composition is discharged over the liquid film may be employed in order to suppress the amount of the composition consumed. Duration of spin coating is not particularly limited but is preferably not more than 180 seconds in terms of throughput. The spin coated substrate may be further treated by edge rinsing or back rinsing to leave no film on the edge portion of the substrate in terms of substrate traveling.

The method used for the heat treatment is not particularly limited. However, the heat treatment may be performed by commonly used methods including heating on a hot plate, heating in a furnace, and heating by light irradiation from a xenon lamp, for example, in a Rapid Thermal Processor (RPT). Heating on a hot plate or in a furnace is preferred. Preferable hot plates that may be used include CLEAN TRACK Series available from Tokyo Electron Ltd., D-Spin Series available from Dainippon Screen Mfg. Co., Ltd. and, SS Series and CS Series available from Tokyo Ohka Kogyo Co., Ltd. Examples of the preferable furnace include Cx-Series (available from Tokyo Electron Co., Ltd.).

Film curing treatment refers to curing the composition on the substrate and imparting the solvent resistance to the film. Heating treatment (baking) is a preferred method for film curing. For example, use may be made of the polymerization reaction during the post-heating of polymerizable groups remaining in the polymer. This post-heating treatment is preferably performed at 100 to 600° C., more preferably at 200 to 500° C. and most preferably at 200° C. to 450° C., preferably for 1 minute to 3 hours, more preferably for 1 minute to 2 hours and most preferably for 1 minute to 1 hour. Such post-heating treatment may be performed in several divided stages.

According to the invention, exposure to high-energy rays such as exposure to light or radiation may be performed instead of heating treatment to trigger the polymerization reaction between the polymerizable groups remaining in the polymer, thus curing the film. Exemplary high-energy rays that may be used include electron rays, UV rays, and X-rays but the film may be cured by other methods.

A film having a dry thickness of about 0.05 to about 1.5 μm in single coating or about 0.1 to about 3 μm in double coating can be formed.

It is preferred for the composition to be substantially free of groups (e.g., hydroxyl group and silanol group) nucleophilically attacking silicon during the production of the composition and the film in order to prevent the cage structure from decomposing during the baking.

(Film Obtained Using Composition for Optical Materials)

The film obtained using the above-described composition for optical materials exhibits a low refractive index. More specifically, the cured film preferably has a refractive index at a wavelength of 633 nm and a measurement temperature of 25° C. of up to 1.34, more preferably 1.27 to 1.34 and most preferably 1.27 to 1.33. At a refractive index within the above-defined range, the cured film is useful as the antireflective film to be referred to later.

The film obtained using the composition for optical materials has many pores in the film and hence exhibits a low refractive index. More specifically, the resulting film has a film density of 0.7 to 1.25 $g/cm^3$, preferably 0.7 to 1.2 $g/cm^3$, and more preferably 0.8 to 1.2 $g/cm^3$. At a film density of less than 0.7 $g/cm^3$, the resulting film may have poor mechanical strength, whereas at a film density exceeding 1.25 $g/cm^3$, the film may have poor heat resistance. The film density may be measured by a known measurement device according to, for example, an X-ray reflectivity (XRR) technique.

The film obtained using the composition for optical materials has small changes in the refractive index and excellent heat resistance under high temperature conditions. More specifically, the resulting film is allowed to stand at a high temperature of 200° C. or more for 2 hours and the refractive index of the film at a wavelength of 633 nm before and after being allowed to stand is determined. The difference of the refractive index obtained by subtracting the refractive index of the film before being allowed to stand from that of the film after being allowed to stand is preferably less than 0.006, more preferably less than 0.004 and most preferably less than 0.002.

The film obtained using the composition for optical materials has small changes in the refractive index and excellent heat resistance under conditions of high temperature and humidity. More specifically, the resulting film is allowed to stand at 110° C. and at a humidity of 95% for 12 hours and the refractive index of the film at a wavelength of 633 nm before and after being allowed to stand is determined. The difference of the refractive index obtained by subtracting the refractive index of the film before being allowed to stand from that of the film after being allowed to stand is preferably 0.01 or less.

The film obtained using the composition for optical materials has excellent adhesion to the substrate on which the film has been formed.

(Antireflective Film)

The film obtained using the above-described composition for optical materials according to the invention is preferably employed as an antireflective film. The film is particularly suitable for use as the antireflective film in optical devices such as microlenses for image sensors, plasma display panels, liquid crystal displays and organic EL displays.

When used as the antireflective film, the film preferably has the lowest possible reflectivity. To be more specific, the average specular reflectivity in a wavelength range of 450 to 650 nm is preferably up to 3%, more preferably up to 2% and most preferably up to 1%. The lower limit is preferably as small as possible and more preferably 0.

The antireflective film preferably has a haze ratio of up to 3%, more preferably up to 1% and most preferably up to 0.5%. The lower limit is preferably as small as possible and more preferably 0.

In cases where the above-described film is used as a monolayer antireflective film, assuming that the transparent substrate has a refractive index nG, the refractive index n of the antireflective film is preferably represented by $\sqrt{nG}$, that is, a square root of the reflective index of the transparent substrate. For example, optical glass has a refractive index of 1.47 to 1.92 at a wavelength of 633 nm and a measurement temperature of 25° C. and the monolayer antireflective film formed on the optical glass preferably has a refractive index n of 1.21 to 1.38. The antireflective film in such a case preferably has a thickness of 10 nm to 10 μm.

When used as a multilayer antireflective film, the above-described film may be used as a low-refractive-index layer and may have under the film a high-refractive-index layer, a hard coat layer and a transparent substrate. A high-refractive-index layer may be directly formed on the substrate without forming a hard coat layer thereon. A medium-refractive-index layer may be further formed between the high-refractive-index layer and the low-refractive-index layer or between the high-refractive-index layer and the hard coat layer.

Each layer of the multilayer antireflective film is described below in detail.

(1) Low-Refractive-Index Layer

The low-refractive-index layer comprises a cured film obtained by curing the inventive composition for optical materials as described above. The refractive index and thickness of the low-refractive-index layer is described.

(i) Refractive Index

The cured film obtained by curing the inventive composition for optical materials, that is, the low-refractive-index film preferably has a refractive index of 1.34 or less at a wavelength of 633 nm and a measurement temperature of 25° C., because the antireflection effect may be considerably reduced when a low-reflective-index film with a refractive index exceeding 1.34 is used in combination with a high-refractive-index film.

Therefore, the low-refractive-index film has a refractive index of more preferably up to 1.33 and even more preferably up to 1.32. In cases where the low-refractive-index film is of a multilayer type, at least one of the layers should have a refractive index which falls within the above-defined range.

In cases where the low-refractive-index layer is formed, the refractive index difference between the high-refractive-index layer and the low-refractive-index layer is preferably at least 0.05 in order to obtain more excellent antireflection effect. When the refractive index difference between the low-refractive-index layer and the high-refractive-index layer is less than 0.05, the synergistic effect of these antireflective film layers is not obtained, which may lead to a reduction in the antireflection effect. The refractive index difference between the low-refractive-index layer and the high-refractive-index layer is more preferably in a range of 0.1 to 0.8 and even more preferably 0.15 to 0.7.

(ii) Thickness

The thickness of the low-refractive-index layer is not particularly limited but is preferably, for example, from 20 to 300 nm. At a thickness of less than 20 nm, the low-refractive-index layer may have reduced adhesion to the underlying high-refractive-index film. On the other hand, at a thickness in excess of 300 nm, interference of light may occur to reduce the antireflection effect. Therefore, the low-refractive-index layer has a thickness of more preferably 20 to 250 nm and even more preferably 20 to 200 nm. In cases where the low-refractive-index layer is of a multilayer structure, the total thickness of the low-refractive-index layer should be from 20 to 300 nm in order to obtain higher antireflection performance.

(2) High-Refractive-Index Layer

The curable composition for use in forming the high-refractive-index layer is not particularly limited but preferably comprises a film-forming component selected from the group consisting of epoxy resins, phenol resins, melamine resins, alkyd resins, cyanate resins, acrylic resins, polyester resins, urethane resins, siloxane resins and combinations of two or more thereof. These resins can be formed into a solid thin film as the high-refractive-index layer, resulting in a considerable improvement of the scratching resistance of the antireflective film.

However, when used alone, these resins usually have a refractive index of 1.45 to 1.62, which may not be sufficient to obtain high antireflection performance. Therefore, the refractive index is preferably adjusted in a range of 1.70 to 2.20 by mixing inorganic particles with a high refractive index such as metal oxide particles. Curable compositions which are curable by application of heat, ultraviolet rays or electron rays may be used for curing but ultraviolet curable compositions having good productivity are used more advantageously.

The thickness of the high-refractive-index layer is not particularly limited but is preferably, for example, from 20 to 30,000 nm. At a thickness of less than 20 nm, the antireflection effect of the high-reflective-index layer and its adhesion to the substrate may be reduced when it is combined with the low-refractive-index layer. On the other hand, at a thickness in excess of 30,000 nm, interference of light may occur to reduce the antireflection effect. Therefore, the high-refractive-index layer has a thickness of more preferably 20 to 1,000 nm and even more preferably 50 to 500 nm. In cases where the high-refractive-index layer is of a multilayer structure, the total thickness of the high-refractive-index layer should be from 20 to 30,000 nm in order to obtain higher antireflection performance. In cases where a hard coat layer is to be formed between the high-refractive-index layer and the substrate, the high-refractive-index layer may have a thickness of 20 to 300 nm.

(3) Hard Coat Layer

The material making up the hard coat layer that may be used in the antireflective film of the invention is not particularly limited. Examples of such material include siloxane resins, acrylic resins, melamine resins, epoxy resins and mixtures of two or more thereof.

The thickness of the hard coat layer is also not particularly limited but is preferably from 1 to 50 μm and more preferably from 5 to 10 μm. At a hard coat layer thickness of less than 1 μm, the adhesion of the antireflective film to the substrate may not be improved, whereas uniform formation of the hard coat layer may be difficult at a thickness in excess of 50 μm.

(4) Substrate

The type of substrate that may be used in the antireflective film of the invention is not particularly limited and examples thereof include transparent substrates made of glass, polycarbonate resins, polyester resins, acrylic resins and triacetyl cellulose (TAC) resins as well as silicon wafers. By forming the antireflective film having any of these substrates, an excellent antireflection effect can be obtained in a wide variety of fields of antireflective films including camera lens portions, TV (CRT) screen display portions, color filters and imaging elements in liquid crystal displays.

The film obtained from the inventive composition for optical materials may also be used as a surface protective film or a phase shift film in optical devices.

EXAMPLES

Next, the present invention is described in further detail by referring to the Examples, which by no means limit the scope of the invention.

The gel permeation column (GPC) measurement was carried out as follows: A Waters 2695 separation module and a Shodex GPC column KF-805L (three columns are directly connected) were used; the column temperature was adjusted to 40° C.; 50 μl of 0.5 wt % tetrahydrofuran solution was introduced; tetrahydrofuran as the eluting solvent was flowed at a flow rate of 1 mL/min; and the sample peaks were detected with an RI detector (Waters 2414) and a UV detector (Waters 2996). The $M_w$ and $M_n$ were calculated using calibration curves prepared with a polystyrene standard.

(Synthesis of Compound I-12)

A mixture solution containing 2000 g of electronic grade concentrated hydrochloric acid, 12 L of n-butanol and 4000 g of ion exchanged water was cooled to 10° C. To this mixture solution was added dropwise a mixture solution containing 840 g of vinyltriethoxysilane and 786 g of methyltriethoxysilane over 20 minutes. Then, the mixture solution was stirred at 25° C. for 18 hours. The precipitated crystals were collected by filtration and washed with 300 mL of electronic grade methanol. After the washing, the crystals were dissolved in 4000 mL of tetrahydrofuran. To the solution were added dropwise 4000 mL of electronic grade methanol, then 8000 mL of ion exchanged water with stirring. The precipitated crystals were collected by filtration and dried to obtain 105 g of a white solid (compound I-12). As a result of $^1$H-NMR measurement (300 MHz, CDC13), multiplet lines were observed at 6.08 to 5.88 ppm and 0.28 to 0.18 ppm, and the vinyl/methyl ratio calculated from the integral ratio was 3.9/4.1. In Formula (1), x=3.9, y=4.1 and x+y=8.0. The resulting silsesquioxane was a mixture of a cage silsesquioxane compound represented by general formula (Q-6).

(Synthesis of Compound I-13)

A mixture solution containing 136 g of electronic grade concentrated hydrochloric acid, 1 L of n-butanol and 395 g of ion exchanged water was cooled to 10° C. To this mixture solution was added dropwise a mixture solution containing 78.3 g of vinyltriethoxysilane and 73.3 g of methyltriethoxysilane over 15 minutes. Then, the mixture solution was stirred at 25° C. for 18 hours. The precipitated crystals were collected by filtration and washed with 100 mL of electronic grade methanol. After the washing, the crystals were dissolved in 500 mL of tetrahydrofuran. To the solution were added dropwise 200 mL of electronic grade methanol, then 200 mL of ion exchanged water with stirring. The precipitated crystals were collected by filtration and dried to obtain 7.8 g of a white solid (compound I-k). As a result of $^1$H-NMR measurement (300 MHz, CDC13), multiplet lines were observed at 6.08 to 5.88 ppm and 0.28 to 0.18 ppm, and the vinyl/methyl ratio calculated from the integral ratio was 4.0/4.0. In Formula (1), x=4.0, y=4.0 and x+y=8.0.

As a result of gas chromatography analysis (analysis conditions: SE-30 capillary column; introduction temperature: 160° C.; the column was kept at 100° C. for 2 minutes and the temperature was then increased at 8° C./min to 260° C.; detector: FID), it was revealed that the resulting silsesquioxane was a mixture consisting primarily of a cage silsesquioxane compound represented by general formula (6) in which the vinyl/methyl ratio was 4/4 (x/y (mol %): 8/0 (1%), 7/1 (2%), 6/2 (11%), 5/3 (22%), 4/4 (28%), 3/5 (22%), 2/6 (11%), 1/7 (3%)). The resulting silsesquioxane was a mixture of a cage silsesquioxane compound represented by general formula (Q-6) as described above.

The content of the cage silsesquioxane compound (A) was 72 mol % with respect to the total amount of the silsesquioxanes.

(Synthesis of Compound I-14)

A mixture solution containing 2000 g of electronic grade concentrated hydrochloric acid, 12 L of n-butanol and 4000 g of ion exchanged water was cooled to 10° C. To this mixture solution was added dropwise a mixture solution containing 944 g of vinyltriethoxysilane and 688 g of methyltriethoxysilane over 20 minutes. Then, the mixture solution was stirred at 25° C. for 18 hours. The precipitated crystals were collected by filtration and washed with 300 mL of electronic grade methanol. After the washing, the crystals were dissolved in 1500 mL of tetrahydrofuran. To the solution were added dropwise 1500 mL of electronic grade methanol, then 1500 mL of ion exchanged water with stirring. The precipitated crystals were collected by filtration and dried to obtain 108 g of a white solid (compound I-14). As a result of $^1$H-NMR measurement (300 MHz, CDC13), multiplet lines were observed at 6.08 to 5.88 ppm and 0.28 to 0.18 ppm, and the vinyl/methyl ratio calculated from the integral ratio was 4.4/3.6. In Formula (1), x=4.4, y=3.6 and x+y=8.0. The resulting silsesquioxane was a mixture of a cage silsesquioxane compound represented by general formula (Q-6).

(Synthesis of Compound I-25)

A mixture solution containing 271 g of electronic grade concentrated hydrochloric acid, 1238 g of n-butanol and 541 g of ion exchanged water was cooled to 10° C. To this mixture solution was added dropwise a mixture solution containing 120 g of vinyltriethoxysilane and 120 g of propyltrimethoxysilane over 10 minutes. Then, the mixture solution was stirred at 25° C. for 18 hours. The precipitated crystals were collected by filtration and washed with 100 mL of electronic grade methanol. After the washing, the crystals were dissolved in 200 mL of tetrahydrofuran. To the solution were added dropwise 217 mL of electronic grade methanol, then 344 mL of ion exchanged water with stirring. The precipitated crystals were collected by filtration and dried to obtain 7 g of a white solid (compound I-25). As a result of $^1$H-NMR measurement (300 MHz, CDC13), multiplet lines were observed at 6.13 to 5.84 ppm, 1.54 to 1.43 ppm, 1.26 to 0.90 ppm and 0.73 to 0.60 ppm, and the vinyl/propyl ratio calculated was 4.0/4.0. In Formula (1), x=4.0, y=4.0 and x+y=8.0. The resulting silsesquioxane was a mixture of a cage silsesquioxane compound represented by general formula (Q-6).

(Synthesis of Compound I-27)

A mixture solution containing 800 g of electronic grade concentrated hydrochloric acid, 3700 g of n-butanol and 1600 g of ion exchanged water was cooled to 10° C. To this mixture solution was added dropwise a mixture solution containing 360 g of vinyltriethoxysilane and 284 g of ethyltrimethoxysilane over 10 minutes. Then, the mixture solution was stirred at 25° C. for 18 hours. The precipitated crystals were collected by filtration and washed with 100 mL of electronic grade methanol. After the washing, the crystals were dissolved in 400 mL of tetrahydrofuran. To the solution were added dropwise 400 mL of electronic grade methanol, then 800 mL of ion exchanged water with stirring. The precipitated crystals were collected by filtration and dried to obtain 31 g of a white solid (compound I-27). As a result of $^1$H-NMR measurement (300 MHz, CDC13), multiplet lines were observed at 6.13 to 5.85 ppm, 1.03 to 0.97 ppm and 0.69 to 0.60 ppm, and the vinyl/methyl ratio calculated was 4.3/3.7. In Formula (1), x=4.3, y=3.7 and x+y=8.0. The resulting silsesquioxane was a mixture of a cage silsesquioxane compound represented by general formula (Q-6).

Other compounds I shown in Table 1 were also synthesized in the same manner by reference to the above-described production examples.

The silsesquioxane of Compound I-4 was a mixture of a cage silsesquioxane compound represented by general formula (Q-2), and the silsesquioxane of Compound I-31 was a mixture of a cage silsesquioxane compound represented by general formula (Q-7).

The silsesquioxanes of Compounds I-1 to I-3 were mixtures of cage silsesquioxane compounds represented by general formula (Q-1), and the silsesquioxane of Compound I-5 was a mixture of a cage silsesquioxane compound represented by general formula (Q-3).

The silsesquioxane of Compound I-6 was a mixture of a cage silsesquioxane compound represented by general formula (Q-4).

The silsesquioxane of Compound I-7 was a mixture of a cage silsesquioxane compound represented by general formula (Q-5).

The silsesquioxanes of Compounds I-8 to I-11 and I-15 to I-30 were mixtures of cage silsesquioxane compounds represented by general formula (Q-6).

The methods of synthesizing polymers (resins A) using the silsesquioxanes (Compounds I) synthesized as above are described below in detail.

(Synthesis of Resin A-13)

The compound synthesized as above (I-13; 5 g) was added to 13.2 g of chlorobenzene. The resulting solution was heated to reflux at an internal temperature of 132° C. under a nitrogen stream and 31 mL of a solution containing 0.2 g of polymerization initiator V601 available from Wako Pure Chemical Industries, Ltd. (10-hour half-life temperature: 66° C.) dissolved in 80 g of chlorobenzene was added dropwise over 310 minutes. After the dropwise addition, the mixture was further heated to reflux for 1 hour. The reaction solution was cooled to room temperature and to the reaction solution were added 340 mL of electronic grade methanol and 34 mL of ion exchanged water. The precipitated solid was collected by filtration and washed with 10 mL of electronic grade methanol. After the washing, the solid was dissolved in 40 g of tetrahydrofuran and 8 g of ion exchanged water was added dropwise with stirring. After the stirring for 1 hour, the supernatant was discarded by decantation and 20 g of electronic grade methanol was added. The precipitated solid was collected by filtration and dried to obtain 1.9 g of a white solid (Resin A-13).

The GPC analysis of the resulting resin revealed that the weight-average molecular weight ($M_w$) was $23.2 \times 10^4$ and the number-average molecular weight ($M_n$) was $10.9 \times 10^4$. The solid contained up to 1 wt % of unreacted compound (I-13) and components with a molecular weight of at least 3,000,000 were not observed. The $^1$H-NMR spectrum was measured using chloroform-d as the measurement solvent and a proton peak derived from methyl group (−0.5 to 0.5 ppm), a proton peak derived from an alkyl group produced by polymerization of vinyl group (0.5 to 3.0 ppm) and a proton peak of remaining vinyl group (4.9 to 6.8 ppm) were observed at an integral ratio of 4.5/1.7/1.8. From the integral ratio, the content of the polymerizable groups in the resin was found to be 22.5 mol % with respect to all organic groups bound to silicon in the resin.

(Synthesis of Resin A-12)

The compound synthesized as above (I-12; 80 g) was added to 2112 g of chlorobenzene. The resulting solution was heated to reflux at an internal temperature of 120° C. under a nitrogen stream and 398 mL of a solution containing 500 mg of polymerization initiator V601 (available from Wako Pure Chemical Industries, Ltd.; 10-hour half-life temperature: 66° C.) dissolved in 200 g of chlorobenzene was added dropwise over 265.3 minutes. After the dropwise addition, the reaction solution was cooled to room temperature and to the reaction solution were added 5200 g of electronic grade methanol and 520 mL of ion exchanged water. The precipitated solid was collected by filtration, washed with 100 mL of electronic grade methanol and dried for 12 hours under reduced pressure. The solid was dissolved in 825 g of tetrahydrofuran and 110 g of ion exchanged water and 110 g of electronic grade methanol were added dropwise with stirring. The precipitated solid was collected by filtration and dried. This operation was repeated three times to obtain 31 g of a white solid (Resin A-12).

The GPC analysis of the resulting resin revealed that the weight-average molecular weight ($M_w$) was $19.3 \times 10^4$ and the number-average molecular weight ($M_n$) was $7.85 \times 10^4$. The solid contained up to 1 wt % of unreacted compound (I-12) and components with a molecular weight of at least 3,000,000 were not observed. The $^1$H-NMR spectrum was measured using chloroform-d as the measurement solvent and a proton peak derived from methyl group (−0.5 to 0.5 ppm), a proton peak derived from an alkyl group produced by polymerization of vinyl group (0.5 to 3.0 ppm) and a proton peak of remaining vinyl group (4.9 to 6.8 ppm) were observed at an integral ratio of 3.5/2.8/1.7. From the integral ratio, the content of the polymerizable groups in the resin was found to be 21.3 mol % with respect to all organic groups bound to silicon in the resin.

(Synthesis of Resin A-25)

The compound (I-25; 4 g) was added to 106 g of chlorobenzene. The resulting solution was heated to reflux at an internal temperature of 120° C. under a nitrogen stream and 15.95 mL of a solution containing 500 mg of polymerization initiator V601 (available from Wako Pure Chemical Industries, Ltd.; 10-hour half-life temperature: 66° C.) dissolved in 200 g of chlorobenzene was added dropwise over 200 minutes. After the dropwise addition, the reaction solution was cooled to room temperature and to the reaction solution were added 200 mL of electronic grade methanol and 20 mL of ion exchanged water. The precipitated solid was collected by filtration, washed with 50 mL of electronic grade methanol and dried for 12 hours under reduced pressure. The solid was dissolved in 75 g of tetrahydrofuran and 9 g of ion exchanged water was added dropwise with stirring. The precipitated solid was collected by filtration and dried to obtain 1.0 g of a white solid (Resin A-25).

The GPC analysis of the resulting resin revealed that the weight-average molecular weight ($M_w$) was $22.3 \times 10^4$ and the number-average molecular weight ($M_n$) was $8.23 \times 10^4$. The solid contained up to 1 wt % of unreacted compound (I-25) and components with a molecular weight of at least 3,000,000 were not observed. The $^1$H-NMR spectrum was measured using chloroform-d as the measurement solvent and a proton peak derived from propyl group, a proton peak derived from an alkyl group produced by polymerization of vinyl group (0.5 to 3.0 ppm) and a proton peak of remaining vinyl group (4.9 to 6.8 ppm) were observed at an integral ratio of 4.0/2.6/1.4. From the integral ratio, the content of the polymerizable groups in the resin was found to be 17.5 mol % with respect to all organic groups bound to silicon in the resin.

Other resins A-1 to A-33 were synthesized by reference to the above-described production examples. The type and composition of silsesquioxane used to synthesize each resin and its weight-average molecular weight and number-average molecular weight are shown in Table 2.

The following abbreviations were used in the table:
BA: butyl acetate
DPE: diphenyl ether
PGMEA: propylene glycol monomethyl ether acetate
TBB: t-butylbenzene
CYHEX: cyclohexanone
CB: chlorobenzene
THF: tetrahydrofuran
V-601: dimethyl 2,2'-azobis(2-methylpropionate) available from Wako Pure Chemical Industries, Ltd.
V-65: 2,2'-azobis(2.4-dimethylvaleronitrile) available from Wako Pure Chemical Industries, Ltd.
VR-110: 2,2'-azobis(2,4,4-trimethylpentane) available from Wako Pure Chemical Industries, Ltd.
V-40: 1,1'-azobis(cyclohexane-1-carbonitrile) available from Wako Pure Chemical Industries, Ltd.
DCP: dicumyl peroxide tion was heated to 120° C. under a nitrogen stream and 50.4 mL of a solution containing 0.47 g of polymerization initiator V601 (available from Wako Pure Chemical Industries, Ltd.; 10-hour half-life temperature: 66° C.) and 113 mg of 2,6-bis (1,1-dimethylethyl)-4-methylphenol dissolved in 235 mL of electronic grade butyl acetate was added dropwise over 80 minutes. After the dropwise addition, the mixture was further stirred at 120° C. for one hour. After the stirring, to the reaction solution were added 3 L of electronic grade methanol and 3 L of ion exchanged water. The precipitated solid was collected by filtration and washed with 100 mL of electronic grade methanol. After the washing, the solid was dissolved in 724 g of tetrahydrofuran. To the solution were added dropwise 50 g of electronic grade methanol, then 150 g of water with stirring. After the stirring for 1 hour, the supernatant was discarded by decantation and 200 g of electronic grade methanol was added. The precipitated solid was collected by filtration and dried to obtain 17.7 g of a white solid (Resin R-1).

The GPC analysis of the resulting resin revealed that the weight-average molecular weight ($M_w$) was $8.7 \times 10^4$ and the number-average molecular weight ($M_n$) was $5.4 \times 10^4$. The solid contained up to 2 wt % of unreacted compound (I—R1) and components with a molecular weight of at least 3,000,000 were not observed. The $^1$H-NMR spectrum was measured using chloroform-d as the measurement solvent and a proton peak derived from an alkyl group produced by polymeriza-

TABLE 2

| Resin A | Recurring unit | Compositional ratio (wt %) | Polymerization solvent | Temperature (° C.) | Initiator | Mw (×10$^4$) | Mn (×10$^4$) |
|---|---|---|---|---|---|---|---|
| A-1 | I-1 | 100 | CB | 132 | V-601 | 20.2 | 8.99 |
| A-2 | I-2 | 100 | CB | 120 | V-601 | 8.06 | 2.99 |
| A-3 | I-3 | 100 | CB | 120 | V-601 | 19.6 | 6.9 |
| A-4 | I-4 | 100 | CB | 120 | V-601 | 8.56 | 3.56 |
| A-5 | I-5 | 100 | CYHEX | 100 | V-65 | 9.88 | 4.56 |
| A-6 | I-6 | 100 | PGMEA | 100 | V-601 | 32.1 | 16.3 |
| A-7 | I-7 | 100 | CB/BA(9/1) | 120 | V-601 | 25.6 | 10.2 |
| A-8 | I-8 | 100 | CB | 120 | V-601 | 20.6 | 8.03 |
| A-9 | I-9 | 100 | CB | 120 | V-601 | 25.3 | 9.66 |
| A-10 | I-10 | 100 | CB | 120 | V-601 | 22.2 | 11.6 |
| A-11 | I-11 | 100 | CB | 120 | V-601 | 23.5 | 12.3 |
| A-12 | I-12 | 100 | CB | 120 | V-601 | 19.3 | 7.85 |
| A-13 | I-13 | 100 | CB | 132 | V-601 | 23.2 | 10.9 |
| A-14 | I-14 | 100 | CB | 120 | V-601 | 19.7 | 9.32 |
| A-15 | I-15 | 100 | CB | 120 | V-601 | 6.54 | 3.66 |
| A-16 | I-16 | 100 | CB | 120 | V-601 | 30.6 | 12.1 |
| A-17 | I-17 | 100 | CB | 120 | V-601 | 16.4 | 10.5 |
| A-18 | I-18 | 100 | CB | 120 | V-601 | 28.6 | 10.6 |
| A-19 | I-19 | 100 | TBB | 150 | VR-110 | 16.5 | 8.62 |
| A-20 | I-20 | 100 | DPE | 120 | V-601 | 26.9 | 10.6 |
| A-21 | I-21 | 100 | CYHEX | 120 | DCP | 16.4 | 8.56 |
| A-22 | I-22 | 100 | DPE | 120 | V-601 | 6.99 | 3.66 |
| A-23 | I-23 | 100 | CB | 80 | V-40 | 10.4 | 5.11 |
| A-24 | I-24 | 100 | CB | 132 | V-601 | 15.6 | 5.01 |
| A-25 | I-25 | 100 | CB | 120 | V-601 | 22.3 | 8.23 |
| A-26 | I-26 | 100 | CB | 100 | V-601 | 9.87 | 4.56 |
| A-27 | I-27 | 100 | CB | 80 | V-601 | 6.55 | 1.96 |
| A-28 | I-28 | 100 | DPE | 120 | V-601 | 23.1 | 8.15 |
| A-29 | I-29 | 100 | DPE | 100 | VR-110 | 48.7 | 15.6 |
| A-30 | I-30 | 100 | BA | 100 | V-601 | 35.1 | 13.3 |
| A-31 | I-31 | 100 | CB | 120 | V-601 | 31.1 | 12.4 |
| A-32 | I-8/I-28 | 50/50 | THF | 60 | V-65 | 9.87 | 3.56 |
| A-33 | I-21/I-25 | 50/50 | CYHEX | 120 | V-601 | 12.33 | 5.95 |

(Synthesis of Comparative Example Resin R-1)

1,3,5,7,9,11,13,15-Octaethenyl-pentacyclo [9.5.1.1$^{3,9}$.1$^{5,15}$.1$^{7,13}$]octasiloxane (cage structure: general formula (Q-6), compound in which 8 substituents R were all vinyl groups; x=8; y=0; Compound I—R1; 50 g) were added to 1320 g of electronic grade butyl acetate. The resulting solution of vinyl group (0.2 to 3.0 ppm) and a proton peak of remaining vinyl group (4.9 to 6.8 ppm) were observed at an integral ratio of 2.6/5.4.

(Synthesis of Comparative Example Resin R-2)

Dodecavinyl-heptacyclo [13.9.1.1$^{3,13}$.1$^{5,11}$.1$^{7,21}$.1$^{9,19}$.1$^{17,23}$]dodecasiloxane (cage structure: general formula (Q-1); compound in which 12 substituents R were all vinyl groups; x=12; y=0) was used to synthesize Comparative Example Resin R-2 ($M_w$=17.8×10$^4$, $M_n$=9.99×10$^4$) in the same manner as Comparative Example Resin R-1.

(Preparation of Composition)

Each of the resins obtained as above was dissolved in a solvent shown in Table 3 to prepare a solution having a solid concentration of 8 wt %. The resulting solution was filtered through a 0.2-μm tetrafluoroethylene filter and applied to a 4-inch silicon wafer by spin coating. The substrate was preliminarily dried at 100° C. for 2 minutes on a hot plate to form a coated film with a thickness of 400 nm.

The resulting coated film was cured by any of the following methods.

(1) Heating

The film was heated at 220° C. for 5 minutes on a hot plate in the atmosphere.

(2) UV Irradiation

A dielectric-barrier discharge excimer lamp UER20-172 available from Ushio Inc. was used to irradiate the coated film with 100 mJ/cm$^2$ of light at a wavelength of 172 nm for 5 minutes on a hot plate at 220° C.

The resulting cured film was evaluated according to the following methods. The results are shown in Table 3.

In Table 3, the content of the surfactant is represented by wt % with respect to the total amount of the composition (coating solution). On the other hand, the content of the adhesion promoter is represented by wt % with respect to the total solids in the composition (coating solution). Surfactants such as BYK307 (BYK Japan KK) and PF6320 (OMNOVA Solutions Inc.) were used. Adhesion promoters such as GPTMS: 3-glycidyloxypropyltrimethoxysilane, MPMDMS: 1-methacryloxypropylmethyldimethoxysilane were used.

(Coated Surface State)

A sample was rated "poor" when occurrence of surface defects such as striations and bumps were visually confirmed and "good" when occurrence of such surface defects was not visually confirmed.

(Refractive Index)

An ellipsometer VASE available from J.A. Woollam Japan Co., Inc. was used to measure the refractive index on a silicon wafer at a wavelength of 633 nm.

(Heat Resistance)

Each sample was heated at 220° C. for 2 hours on a hot plate in the atmosphere. A sample was rated "excellent" when the refractive index difference between before and after the test was less than 0.002, "good" when the refractive index difference was at least 0.002 but less than 0.004, "fair" when the refractive index difference was at least 0.004 but less than 0.006, and "poor" when the refractive index difference was at least 0.006. From a practical point of view, no sample should be rated "poor" as for the heat resistance.

(Adhesion)

The film surface was scratched with a diamond pen so as to form 5×5 squares with a size of 3×3 mm. All the squares were covered with a 3M Scotch tape (No. 610) and it was carefully adhered to the film surface so as to prevent bubbles from entering. Then, the tape was peeled off in a vertical direction and the test for adhesion to the silicon substrate was conducted. A sample was rated "poor" when delamination occurred at one or more of the 25 squares and "good" when no delamination occurred.

TABLE 3

| | Resin | Solvent | Surfactant (0.01 wt %) | Adhesion promoter (0.01 wt %) | Curing method | Coated surface state | Refractive index | Heat resistance | Adhesion |
|---|---|---|---|---|---|---|---|---|---|
| EX 1 | A-1 | PGMEA | — | — | Heating | Good | 1.321 | Fair | Good |
| EX 2 | A-2 | PGMEA | — | — | Heating | Good | 1.323 | Excellent | Good |
| EX 3 | A-3 | PGMEA | — | — | Heating | Good | 1.326 | Fair | Good |
| EX 4 | A-4 | PGMEA | PF6320 | — | Heating | Good | 1.319 | Good | Good |
| EX 5 | A-5 | CYHEX | — | — | Heating | Good | 1.320 | Fair | Good |
| EX 6 | A-6 | PGMEA | — | — | UV irradiation | Good | 1.330 | Excellent | Good |
| EX 7 | A-7 | CYHEX | — | MPMDMS | Heating | Good | 1.310 | Fair | Good |
| EX 8 | A-8 | PGMEA | — | — | Heating | Good | 1.322 | Excellent | Good |
| EX 9 | A-9 | PGMEA | — | — | Heating | Good | 1.321 | Excellent | Good |
| EX 10 | A-10 | PGMEA | — | — | Heating | Good | 1.294 | Excellent | Good |
| EX 11 | A-11 | PGMEA | — | — | Heating | Good | 1.293 | Excellent | Good |
| EX 12 | A-12 | PGMEA | — | — | Heating | Good | 1.290 | Excellent | Good |
| EX 13 | A-13 | PGMEA | — | — | Heating | Good | 1.293 | Excellent | Good |
| EX 14 | A-14 | PGMEA | — | — | Heating | Good | 1.297 | Excellent | Good |
| EX 15 | A-15 | PGMEA | BYK307 | — | UV irradiation | Good | 1.310 | Good | Good |
| EX 16 | A-16 | PGMEA | — | — | Heating | Good | 1.313 | Fair | Good |
| EX 17 | A-17 | PGMEA | — | — | Heating | Good | 1.316 | Excellent | Good |
| EX 18 | A-18 | CYHEX | — | GPTMS | Heating | Good | 1.329 | Excellent | Good |
| EX 19 | A-19 | PGMEA | — | — | Heating | Good | 1.333 | Excellent | Good |
| EX 20 | A-20 | PGMEA | — | — | Heating | Good | 1.315 | Excellent | Good |
| EX 21 | A-21 | CYHEX | — | — | Heating | Good | 1.302 | Excellent | Good |
| EX 22 | A-22 | PGMEA | — | — | Heating | Good | 1.301 | Excellent | Good |
| EX 23 | A-23 | PGMEA | — | — | UV irradiation | Good | 1.314 | Excellent | Good |
| EX 24 | A-24 | PGMEA | — | — | Heating | Good | 1.319 | Excellent | Good |
| EX 25 | A-25 | PGMEA | — | — | Heating | Good | 1.316 | Excellent | Good |
| EX 26 | A-26 | PGMEA | — | — | Heating | Good | 1.310 | Excellent | Good |
| EX 27 | A-27 | CYHEX | PF6320 | — | Heating | Good | 1.316 | Excellent | Good |
| EX 28 | A-28 | PGMEA | — | — | Heating | Good | 1.326 | Excellent | Good |
| EX 29 | A-29 | PGMEA | — | — | Heating | Good | 1.320 | Excellent | Good |
| EX 30 | A-30 | PGMEA | — | — | Heating | Good | 1.329 | Excellent | Good |

TABLE 3-continued

| | Resin | Solvent | Surfactant (0.01 wt %) | Adhesion promoter (0.01 wt %) | Curing method | Coated surface state | Refractive index | Heat resistance | Adhesion |
|---|---|---|---|---|---|---|---|---|---|
| EX 31 | A-31 | BA | — | — | Heating | Good | 1.321 | Excellent | Good |
| EX 32 | A-32 | PGMEA | — | — | Heating | Good | 1.319 | Excellent | Good |
| EX 33 | A-33 | PGMEA | — | — | Heating | Good | 1.320 | Excellent | Good |
| CE 1 | R-1 | PGMEA | — | — | Heating | Good | 1.351 | Poor | Poor |
| CE 2 | R-2 | PGMEA | — | — | Heating | Good | 1.349 | Poor | Poor |

The results in Table 3 confirmed that, when the inventive composition for optical materials is used, a film having a low refractive index and excellent temporal refractive index stability under high temperature conditions and also having excellent adhesion is obtained by curing processes such as heating and UV irradiation. In particular, films exhibiting a lower refractive index and more excellent heat resistance were obtained in Examples 10 to 14.

On the other hand, when the polymers obtained from the silsesquioxanes which did not satisfy formula (1) were used, the resulting films had a comparatively high refractive index and poor heat resistance and adhesion.

(Moisture Resistance)

Each sample was allowed to stand at a temperature of 110° C. and a humidity of 95% for 12 hours to measure the change of the refractive index between before and after the test. The refractive index changes in Examples 9, 10, 11, 12, 13, 14, 15 and 16 were all less than 0.01 and were rated "good" but the refractive index changes in Comparative Examples 1 and 2 were 0.01 or more and were rated NG.

(Density)

The density was also evaluated as described below.

An X-ray reflectivity (XRR) technique was used to measure the density of the resulting cured films. The films in Examples 12, 13, 14 and 15 had densities of 0.87 g/cm$^3$, 0.92 g/cm$^3$, 0.98 g/cm$^3$ and 1.15 g/cm$^3$, respectively. The films in Comparative Examples 1 and 2 had densities of 1.35 g/cm$^3$ and 1.29 g/cm$^3$, respectively.

Examples are described below in detail for the cases where the pore forming agent was used.

(Synthesis of Resin B-1)

PGMEA (4 g) was put in a three-necked flask under a nitrogen stream and heated to 80° C. Then, to the reaction solution was added dropwise a solution containing 10 g of 1-ethyl-cyclopentyl methacrylate and 0.379 g of polymerization initiator V-601 (Wako Pure Chemical Industries, Ltd.) dissolved in 36 g of PGMEA over 2 hours. After the dropwise addition, the mixture was further reacted at 80° C. for 1 hour. The reaction solution was allowed to cool and added dropwise to 500 mL of methanol over 10 minutes. The precipitated power was collected by filtration and dried to obtain 5.83 g of Resin (B-1).

The GPC analysis of the resulting resin revealed that the weight-average molecular weight ($M_w$) was 16200 and the number-average molecular weight ($M_n$) was 9800. As a result of thermogravimetric analysis (SDT Q600 available from TA Instruments was used; nitrogen flow rate: 100 mL/min; the temperature was increased at a temperature elevation rate of 20° C./min), the 50% weight loss temperature was 228° C.

Resins B-2 to B-4 were synthesized by reference to the above-described production examples.

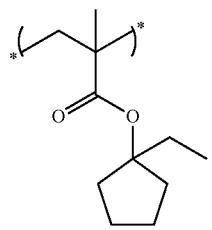
(B-1)

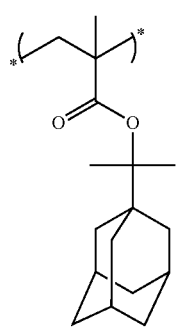
(B-2)

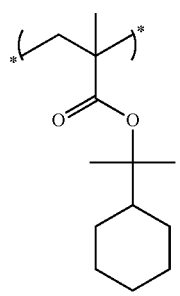
(B-3)

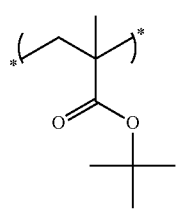
(B-4)

(Synthesis of Resin B-5)

Cyclohexanedimethanol (3.6 g) and butanediol divinyl ether (3.6 g) were dissolved in 5 mL of tetrahydrofuran. To the solution was added 100 mg of p-toluenesulfonic acid pyridine salt and the mixture was stirred at room temperature for 4 hours. After the stirring, 0.5 mL of triethylamine was added, 100 mL of methanol was added to the reaction solution and the mixture was stirred for 30 minutes. After the stirring, of the separated two layers, the upper layer was removed and the lower layer was dried under reduced pressure to obtain Resin (B-5) made of a transparent viscous liquid in an amount of 2.8 g. The GPC analysis of the resulting resin revealed that the weight-average molecular weight ($M_w$) was 14000 and the number-average molecular weight ($M_n$) was 3500. As a result of thermogravimetric analysis (SDT Q600 available from TA Instruments was used; nitrogen flow rate: 100 mL/min; the temperature was increased at a temperature elevation rate of 20° C./min), the 50% weight loss temperature was 241° C.

Polyacetals B-6 to B-8 were synthesized by reference to the above-described production examples.

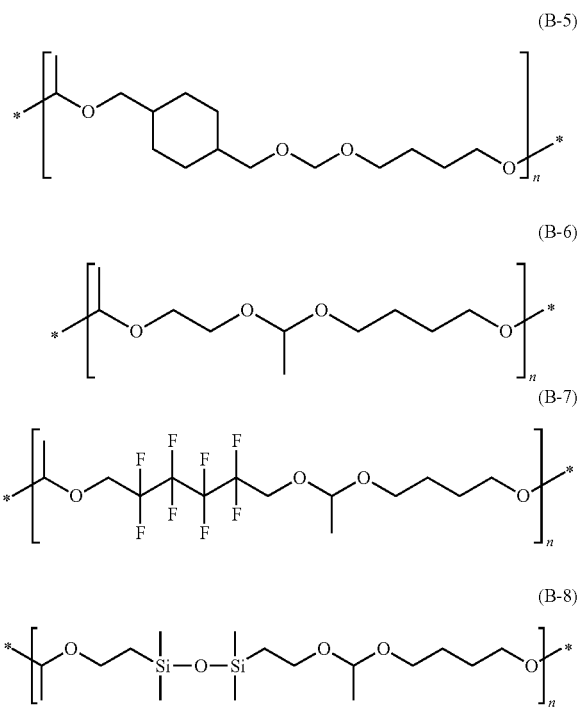

The polystyrene-equivalent number-average molecular weight and the 50% weight loss temperature in the thermogravimetric analysis of Resins (B-1) to (B-8) synthesized as above and polyalkylene glycols (B-9) to (B-13) available from Aldrich were shown in Table 4.

filter and applied to a 4-inch silicon wafer by spin coating. The substrate was preliminarily dried at 100° C. for 2 minutes on a hot plate to form a coated film with a thickness of 400 nm.

The resulting coated film was cured by any of the following methods.

(1) Heating

The film was heated at 220° C. for 5 minutes on a hot plate in the atmosphere.

(2) UV Irradiation

A dielectric-barrier discharge excimer lamp UER20-172 available from Ushio Inc. was used to irradiate the coated film with 100 mJ/cm² of light at a wavelength of 172 nm for 5 minutes on a hot plate at 220° C.

The resulting cured film was evaluated according to the following methods. The results are shown in Table 5.

In Table 5, the content of the surfactant is represented by wt % with respect to the total amount of the composition (coating solution). On the other hand, the contents of the adhesion promoter and pore forming agent are represented by wt % with respect to the total solids in the composition (coating solution). The surfactant used was PF6320 (OMNOVA Solutions Inc.). The adhesion promoter used was GPTMS: 3-glycidyloxypropyltrimethoxysilane.

(Film Thickness Reduction Ratio During Film Curing)

The ellipsometer VASE available from J.A. Woollam Japan Co., Inc. was used to measure the thickness of the film after preliminary drying and that of the cured film and the film thickness reduction ratio was calculated by the following equation:

Film thickness reduction ratio(%)=(thickness of the film after preliminary drying−thickness of the cured film)/thickness of the film after preliminary drying×100

A sample was rated "good" at a film thickness reduction ratio of less than 2.0% and "poor" at a film thickness reduction ratio of 2.0% or more.

TABLE 4

| Pore forming agent | Weight-average molecular weight | Number-average molecular weight | 50% weight loss temperature (° C.) |
|---|---|---|---|
| B-1 | 16200 | 9800 | 228 |
| B-2 | 5100 | 2400 | 232 |
| B-3 | 20500 | 11200 | 245 |
| B-4 | 19200 | 10200 | 262 |
| B-5 | 14000 | 3500 | 241 |
| B-6 | 10500 | 1900 | 191 |
| B-7 | 21000 | 3800 | 251 |
| B-8 | 7000 | 2500 | 298 |
| B-9: Polyethylene glycol | — | 200 | 271 |
| B-10: Polyethylene glycol dimethyl ether | — | 250 | 281 |
| B-11: Polyethylene glycol monobutyl ether | — | 200 | 264 |
| B-12: Polypropylene glycol | — | 200 | 275 |
| B-13: Polypropylene glycol monobutyl ether | — | 250 | 298 |

(Preparation of Composition)

One of the resins obtained as above and a pore forming agent were dissolved in a solvent shown in Table 5 to prepare a solution having a solid concentration of 8 wt %. The resulting solution was filtered through a 0.2-μm tetrafluoroethylene (Coated Surface State)

A sample was rated "poor" when occurrence of surface defects such as striations and bumps was visually confirmed and "good" when occurrence of such surface defects was not visually confirmed.

TABLE 5

| | Resin | Solvent | Surfactant (0.01 wt %) | Adhesion promoter (0.01 wt %) | Pore forming agent | Amount of pore forming agent added (wt %) | Curing method | Refractive index | Film thickness reduction ratio (%) | Coated surface state |
|---|---|---|---|---|---|---|---|---|---|---|
| EX 34 | A-1 | PGMEA | — | — | B-5 | 20 | Heating | 1.311 | Good | Good |
| EX 35 | A-2 | PGMEA | — | — | B-2 | 25 | Heating | 1.303 | Good | Good |
| EX 36 | A-3 | PGMEA | — | — | B-7 | 10 | Heating | 1.315 | Good | Good |
| EX 37 | A-6 | PGMEA | — | — | B-4 | 20 | Heating | 1.311 | Good | Good |
| EX 38 | A-12 | PGMEA | — | — | B-1 | 20 | Heating | 1.286 | Good | Good |
| EX 39 | A-12 | PGMEA | — | — | B-3 | 20 | Heating | 1.285 | Good | Good |
| EX 40 | A-12 | PGMEA | — | — | B-9 | 20 | Heating | 1.288 | Good | Good |
| EX 41 | A-14 | PGMEA | — | — | B-12 | 20 | Heating | 1.282 | Good | Good |
| EX 42 | A-16 | PGMEA | — | — | B-9 | 20 | Heating | 1.300 | Good | Good |
| EX 43 | A-16 | PGMEA | — | — | B-6 | 25 | Heating | 1.299 | Good | Good |
| EX 44 | A-18 | CYHEX | — | GPTMS | B-11 | 20 | Heating | 1.310 | Good | Good |
| EX 45 | A-19 | PGMEA | — | — | B-8 | 20 | Heating | 1.315 | Good | Good |
| EX 46 | A-30 | PGMEA | PF6320 | — | B-13 | 20 | UV irradiation | 1.311 | Good | Good |
| EX 47 | A-16 | PGMEA | — | — | B-10 | 20 | Heating | 1.309 | Good | Good |

The above results revealed that a film with a lower refractive index can be obtained by further incorporating a pore forming agent in the composition for optical materials according to the invention. It was also revealed that the thickness of the resulting film is less reduced during the curing and the film is excellent in practical use.

Examples on the application of the film obtained from the composition for optical materials according to the invention to antireflective films are described below in detail.

(Reflectivity)

The average specular reflectivity (%) at 450 to 650 nm at an angle of incidence of 5° was measured with a spectrophotometer available from JASCO Corporation.

[Manufacture of Antireflective Film 1]

Solutions were prepared by changing the solid concentration of the compositions in Examples 12, 13, 14 and Comparative Example 1 to 4 wt %. The resulting solutions were filtered through a 0.2-μm tetrafluoroethylene filter and applied to a 1-mm glass slide by spin coating. The substrate was preliminarily dried at 100° C. for 2 minutes on a hot plate. The coating was further heated at 220° C. for 5 minutes on the hot plate to form a coated film with a thickness of 200 nm.

The reflectivity was measured in cases where the compositions in Examples 12, 13, 14 and Comparative Example 1 prepared as above were used. Reflectivities (%) of 0.5%, 0.5%, 0.6% and 3.5% were obtained, respectively.

[Manufacture of Antireflective Film 2]

RASA TI available from RASA Industries, Ltd. was applied to a silicon wafer by spin coating and the coating was baked at 350° C. to form a film with a thickness of 60 nm and a refractive index of 2.0. The concentration of the composition in Examples 12 was adjusted and the composition was applied so as to have a film thickness after baking of 20 nm. The substrate was heated on a hot plate at 100° C. for 2 minutes, then at 220° C. for 5 minutes to form a multilayer antireflective film.

The composition in Comparative Example 1 was used instead of the composition in Example 12 and the same operation was repeated to form a multilayer antireflective film.

As a result of the reflectivity measurement, the reflectivity was 1.8% when using the composition in Example 12 and 4.4% when using the composition in Comparative Example 1.

What is claimed is:

1. A composition for optical materials comprising a polymer obtained from silsesquioxanes which are represented by average composition formula (1):

$$(R^1SiO_{1.5})_x(R^2SiO_{1.5})_y \quad \text{Formula (1)}$$

wherein $R^1$ is a polymerizable group, $R^2$ is a non-polymerizable group, x is a number of 2.0 to 14.0, y is a number of 2.0 to 14.0, provided that x+y=8.0 to 16.0, and $R^1$ groups and $R^2$ groups may be the same or different and comprise at least one cage silsesquioxane compound.

2. The composition for optical materials according to claim 1, wherein the at least one cage silsesquioxane compound is represented by formula (2):

$$(RSiO_{1.5})_a \quad \text{Formula (2)}$$

wherein each R is independently a polymerizable group or a non-polymerizable group, a is an integer of 8, 10, 12, 14 or 16, provided that R groups may be the same or different.

3. The composition for optical materials according to claim 2, wherein the silsesquioxanes comprise the at least one cage silsesquioxane compound selected from the group consisting of cage silsesquioxane compounds represented by general formulas (Q-1) to (Q-7):

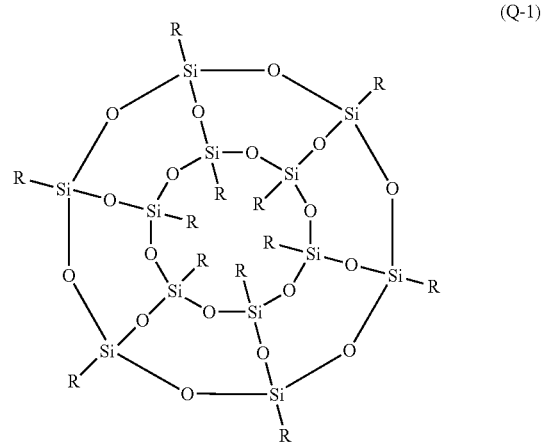

(Q-1)

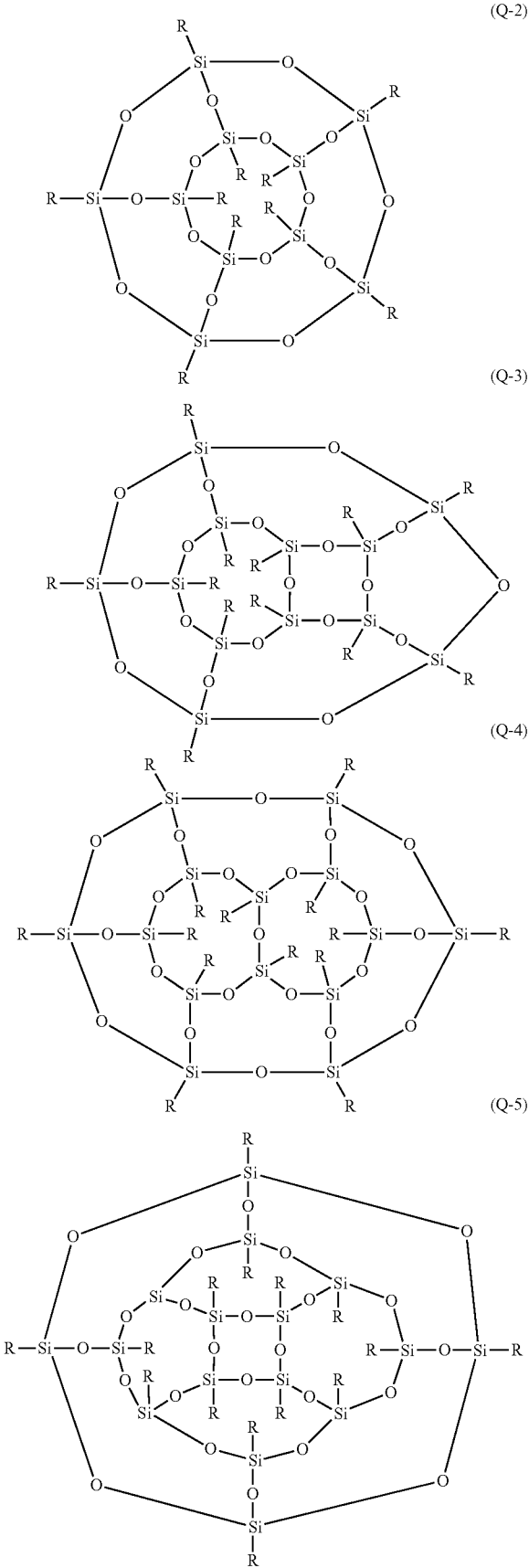

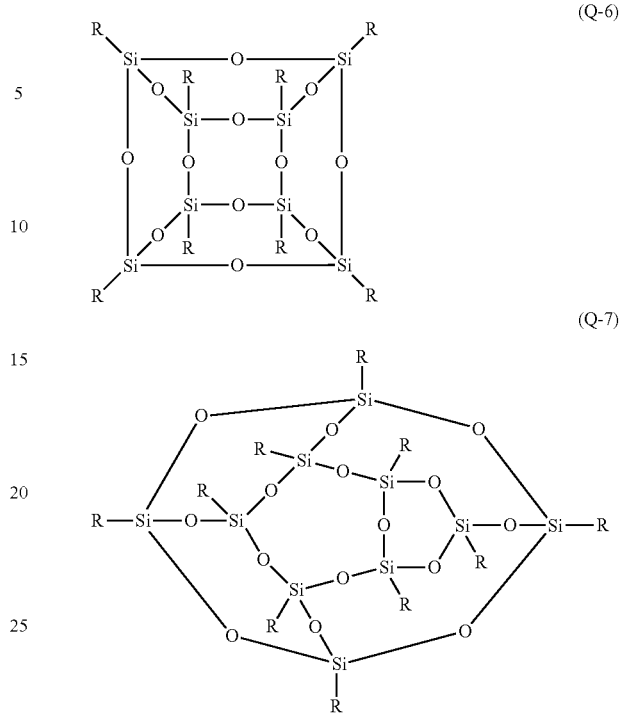

wherein each R is independently a polymerizable group or a non-polymerizable group.

4. The composition for optical materials according to claim 3, wherein the silsesquioxanes are represented by formula (1) in which x is a number of 2.0 to 6.0 (2.0≦x≦6.0), y is a number of 2.0 to 6.0 (2.0≦y≦6.0) and x+y=8, and comprise the at least one cage silsesquioxane compound represented by general formula (Q-6).

5. The composition for optical materials according to claim 1, wherein the at least one cage silsesquioxane compound comprises a cage silsesquioxane compound (A) having at least three polymerizable groups and at least three non-polymerizable groups.

6. The composition for optical materials according to claim 5, wherein the compound (A) is contained in an amount of at least 10 mol % with respect to the total amount of the silsesquioxanes.

7. The composition for optical materials according to claim 1, wherein the polymer has a weight-average molecular weight of 10,000 to 500,000.

8. The composition for optical materials according to claim 1 further comprising a pore forming agent.

9. The composition for optical materials according to claim 8, wherein the pore forming agent is at least one selected from the group consisting of polystyrene, polyalkylene oxide, polylactic acid, polycaprolactone, polycaprolactam, polyurethane, polyacrylate, polyacrylic acid, polymethacrylate, polymethacrylic acid, polyacetal and polyperoxide.

10. The composition for optical materials according to claim 8, wherein the pore forming agent has a 50% weight loss temperature of 180 to 350° C. in thermogravimetric analysis under a nitrogen stream at a temperature elevation rate of 20° C./min.

11. The composition for optical materials according to claim 8, wherein the pore forming agent has a polystyrene-equivalent number-average molecular weight of 100 to 50,000.

12. A film obtained using the composition for optical materials according to claim 1.

13. The film according to claim 12 having a refractive index of up to 1.34.

14. The film according to claim 12 having a film density of 0.7 to 1.25 g/cm³.

15. The film according to claim 12 used as an antireflective film.

16. An optical device having the film according to claim 12.

17. A polymer obtained from silsesquioxanes which are represented by average composition formula (1):

$$(R^1SiO_{1.5})_x(R^2SiO_{1.5})_y \qquad \text{Formula (1)}$$

wherein $R^1$ is a polymerizable group, $R^2$ is a non-polymerizable group, x is a number of 2.0 to 14.0, y is a number of 2.0 to 14.0, provided that x+y=8.0 to 16.0, and $R^1$ groups and $R^2$ groups may be the same or different and comprise at least one cage silsesquioxane compound.

18. The composition for optical materials according to claim 1, wherein unreacted polymerizable groups derived from the silsesquioxanes remain in an amount of 30 to 90 mol % in the polymer.

19. The composition for optical materials according to claim 1, wherein the polymer is obtained by polymerization of the silsesquioxanes in the presence of an organic azo compound as a polymerization initiator.

20. The composition for optical materials according to claim 1 further comprising a surfactant.

\* \* \* \* \*